United States Patent
Chen et al.

(10) Patent No.: US 10,787,699 B2
(45) Date of Patent: Sep. 29, 2020

(54) GENERATING PLURALITIES OF PRIMER AND PAYLOAD DESIGNS FOR RETRIEVAL OF STORED NUCLEOTIDES

(71) Applicant: Microsoft Technology Licensing, LLC, Redmond, WA (US)

(72) Inventors: Yuan-Jyue Chen, Seattle, WA (US); Karin Strauss, Seattle, WA (US); Luis H. Ceze, Seattle, WA (US); Siena Dumas Ang, Seattle, WA (US); Sergey Yekhanin, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 786 days.

(21) Appl. No.: 15/427,808

(22) Filed: Feb. 8, 2017

(65) Prior Publication Data
US 2018/0223341 A1    Aug. 9, 2018

(51) Int. Cl.
*C12Q 1/6811* (2018.01)
*G16B 25/00* (2019.01)

(52) U.S. Cl.
CPC ............ *C12Q 1/6811* (2013.01); *G16B 25/00* (2019.02)

(58) Field of Classification Search
None
See application file for complete search history.

(56) References Cited

U.S. PATENT DOCUMENTS

| | | |
|---|---|---|
| 6,828,098 B2 | 12/2004 | Langmore et al. |
| 7,194,504 B2 | 3/2007 | Moulton |
| 8,769,689 B2 | 7/2014 | Hoglund |
| 8,806,127 B2 | 8/2014 | Brownell et al. |
| 2008/0131886 A1 | 6/2008 | Ji et al. |
| 2014/0236490 A1 | 8/2014 | Van Rooyen et al. |
| 2018/0223340 A1 | 8/2018 | Chen et al. |

FOREIGN PATENT DOCUMENTS

| | | |
|---|---|---|
| EP | 1136932 A1 | 9/2001 |
| WO | 2013178801 A2 | 12/2013 |
| WO | 2015144858 A1 | 10/2015 |
| WO | 2016164779 A1 | 10/2016 |

OTHER PUBLICATIONS

Martin, Luther, "Collisions in a hash function from DNA testing", Published on: Jun. 19, 2012 Available at: https://www.voltaga.com/security/collisions-in-a-hash-function-from-dna-testing/.
Georgescu, et al., "Mechanism of polymerase collision release from sliding clamps on the lagging strand", In Journal of European Molecular Biology Organization, vol. 28, Issue 19, Aug. 20, 2009, pp. 2981-2991.
Simmler, et al., "Real-Time Primer Design for DNA Chips", In Proceedings of Second IEEE International Workshop on High Performance Computational Biology, Apr. 22, 2003, 8 pages.
Fan, Shelly, "This Droplet of DNA Could Store 600 Smartphones Worth of Retrievable Data", Published on: Apr. 17, 2016 Available at: http://singularityhub.com/2016/04/17/this-droplet-of-dna-could-store-600-smartphones-worth-of-retrievable-data/.
De Simone, Sergio, "Microsoft Experimenting with Using Synthetic DNA for Digital Data Storage", Published on: May 1, 2016 Available at: https://www.infoq.com/news/2016/05/microsoft-dna-storage.
Church, et al., "Next-Generation Digital Information Storage in DNA", In Journal of Science, vol. 337, Aug. 16, 2012, pp. 1-2.
Goldman, et al., "Towards practical, high-capacity, low-maintenance information storage in synthesized DNA", In Journal of Nature, vol. 494, Feb. 7, 2013, pp. 77-80.
Yazdi, et al., "A Rewritable, Random-Access DNA-Based Storage System", In Journal of Scientific Reports, vol. 5, Sep. 18, 2015, pp. 1-10.
Bornholt, et al., "A DNA-Based Archival Storage System", In Proceedings of 21th ACM International Conference on Architectural Support for Programming Languages and Operating Systems, Apr. 2, 2016, 13 pages.
"PCR Primer Design Guidelines", Retrieved from https://web.archive.org/web/20161221065135/http://www.premierbiosoft.com/tech_notes/PCR_Primer_Design.html, Dec. 21, 2016, 3 Pages.
"Primer3Plus", http://www.bioinformatics.nl/cgi-bin/primer3plus/primer3plus.cgi, Dec. 2, 2008, 1 Page.
Ye, et al., "Primer-BLAST: A Tool to design target-specific primers for polymerase chain reaction", In BMC Bioinformatics, vol. 13, Issue 1, Jun. 18, 2012, 11 Pages.
"Interational Search Report Issued in PCT Application No. PCT/US2018/016327", dated May 7, 2018, 13 Pages.
"International Search Report & Written Opinion Issued in PCT Application No. PCT/US2018/016530", dated Jun. 4, 2018, 16 Pages.
"Non Final Office Action Issued in U.S. Appl. No. 15/427,344", dated Feb. 6, 2020, 10 Pages.

*Primary Examiner* — G Steven Vanni
(74) *Attorney, Agent, or Firm* — Newport IP, LLC; Benjamin Keim

(57) ABSTRACT

This disclosure describes techniques to improve the accuracy of random access of data stored in polynucleotide sequence data storage systems. Primers used in polynucleotide sequence replication and amplification can be scored against a number of criteria that indicate the fitness of sequences of nucleotides to function as primers. Primers having scores that indicate a particular fitness to function as primers can be added to a specific group of primers. The primers from the group of primers can be used in amplification and replication of polynucleotide sequences that encode digital data. Additionally, an amount of overlap between primer targets and payloads encoding digital data can be determined. Minimizing the amount of overlap between primer targets and payloads can improve the efficiency of polynucleotide replication and amplification. The bits of the digital data can be randomized to minimize the amount of overlap between payloads encoding the digital data and primer targets.

20 Claims, 6 Drawing Sheets
Specification includes a Sequence Listing.

AGTAGGCTA ... C

| | First Position - A | Second Position - G | Nth Position - C |
|---|---|---|---|
| Secondary Structure | 0 | 0 | 1 |
| Primer-Dimer Formation | 0 | 0 | 0 |
| Length of A/T Regions | 0 | 0 | 0 |
| Length of G/C Regions | 0 | 1 | 0 |
| GC Content | 0 | 1 | 1 |
| Melting Temperature | 0 | 1 | 1 |
| Nucleotide Differentiation | 0 | 0 | 0 |

FIG. 3

GENERATING PLURALITIES OF PRIMER AND PAYLOAD DESIGNS FOR RETRIEVAL OF STORED NUCLEOTIDES

BACKGROUND

Polynucleotide sequences can be arranged in a linear chain of organic molecules that are nitrogen-containing bases, such as adenine (A), guanine (G), thymine (T), cytosine (C), in the case of deoxyribonucleic acid (DNA) and T, G, C, and uracil (U), in the case of ribonucleic acid (RNA). Polynucleotide sequences can be naturally-occurring or synthetic. In some cases, individual bases included in a polynucleotide sequence can pair with a complementary base in another polynucleotide sequence to produce a double stranded arrangement of polynucleotide sequences. For example, in the case of deoxyribonucleic acid (DNA), T's and A's are complementary and G's and C's are complementary. In the case of ribonucleic acid (RNA), T's and U's are complementary and G's and C's are complementary.

Complementary nucleotides in two polynucleotide sequences can align with one another to form a double stranded polynucleotide. The two ends of a polynucleotide sequence, referred to as the 5' and 3' ends, are chemically different. Polynucleotide sequences are conventionally represented starting with the 5' nucleotide end at the left. The interactions between different strands are predictable based on sequence: two single strands can bind to each other and form a double helix if they are complementary. The two strands in a double helix have opposite directionality (5' end attached to the other strand's 3' end), and thus the two sequences are the "reverse complement" of each other. Two strands do not need to be fully complementary to bind to one another.

Polynucleotide sequence replication can utilize enzymes, often referred to as "polymerases", that attach to a portion of a polynucleotide sequence and produce a complementary strand of that polynucleotide sequence. For example, a polymerase can attach to a primer bound to a target area on an end of a polynucleotide sequence and move along the chain of nucleotides by identifying an individual nucleotide in the chain, generating a complementary nucleotide, and repeating the process with the next nucleotide in the sequence. Polynucleotide replication techniques can be used to produce thousands of double stranded polynucleotide sequences from a single polynucleotide sequence.

In some situations, interactions between nucleotides included in a polynucleotide sequence can cause the linear chain to lose its structure and become arranged in a secondary structure. For example, portions of a polynucleotide sequence can fold to produce loops or hairpin structures. The formation of secondary structures for polynucleotide sequences can interfere with the replication of these polynucleotide sequences. Additionally, the duplication of a binding site for a primer at a location other than an end of the nucleotide sequence can result in errors in double stranded polynucleotide sequences produced during the replication process. To illustrate, some double stranded polynucleotide sequences produced during the replication process can be incomplete and/or do not correspond to the template polynucleotide sequence.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Digital data can be encoded as a series of nucleotides and one or more polynucleotide sequences can be generated that encode the digital data. The portion of the polynucleotide sequence that includes an arrangement of nucleotides that corresponds to the digital data can be referred to herein as the "payload." In addition to including the payload, a polynucleotide sequence can also include other regions that included additional arrangements of nucleotides that can be used to encode other information. The additional information can include addressing information used to reassemble binary data decoded from multiple polynucleotide sequences. A polynucleotide sequence can also include arrangements of bases that can be used for other purposes. For example, a polynucleotide sequence can include a region that includes nucleotides used in relation to polynucleotide sequence replication techniques. In some cases, a region of a polynucleotide sequence to which a primer can bind during a polynucleotide replication technique can be referred to herein as a "primer target." A primer is a sequence of nucleotides that can bind to the primer target and a polymerase can utilize the primer as a starting point to replicate nucleotides of a target sequence. A primer and a corresponding primer target have complementary sequences of nucleotides.

The primers can be evaluated using a number of criteria that can indicate fitness to be used as a starting sequence for synthesizing a complementary polynucleotide sequence as part of polynucleotide replication. The evaluation criteria can correspond to secondary structure formation, amount of G/C content, melting temperature, length of A/T regions, length of G/C regions, primer-dimer formation, similarity of nucleotide sequences of the primers to other nucleotide sequences that may be present, or combinations thereof. For example, a number of characteristics of a primer can be evaluated against the evaluation criteria. In some scenarios, individual nucleotides of a primer can be scored according to the evaluation criteria. The scores of the individual nucleotides can be aggregated and compared against a threshold. In situations where the aggregate score for a primer is less than the threshold score, the primer can be added to a group of primers that can be used in generating polynucleotide sequences that can be replicated.

Polynucleotide sequences can be generated that include a payload and at least one primer target that corresponds with a primer from a group of primers that are fit for use in polynucleotide replication. A primer associated with a payload can be identified such that an amount of overlap between the sequence of nucleotides in the primer target and one or more portions of the sequence of nucleotides of the payload is minimized. Additionally, in some instances, the amount of overlap between the sequence of the primer target and the sequences of a group of payloads can be minimized. The amount of overlap can be determined by comparing the sequence of nucleotides included in the primer target with various regions of nucleotides in the payload. In various implementations, the amount of overlap can indicate an amount of sequence identity between the primer target sequence and the payload sequence. In situations where the amount of overlap between the sequence of nucleotides of a primer target and the sequence of nucleotides of at least one region of the payload is greater than a threshold amount, one or more remedial actions can be performed. To illustrate, another primer can be associated with the payload and an additional comparison can be made between the sequence of nucleotides of a new primer target that correspond to the new primer and the nucleotides of regions of the payload to determine any regions of overlap. In another implementation, the binary data that is encoded by the payload can be randomized and a new sequence of nucleotides can be generated for the payload and compared with the primer to determine whether the amount of overlap between the sequence of nucleotides of the primer target and regions of the new sequence of nucleotides of the payload is less than the threshold amount of overlap.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIG. 3 shows a table that includes example scoring for nucleotides included in a primer according to a number of primer evaluation criteria.

DETAILED DESCRIPTION

Figure 1:
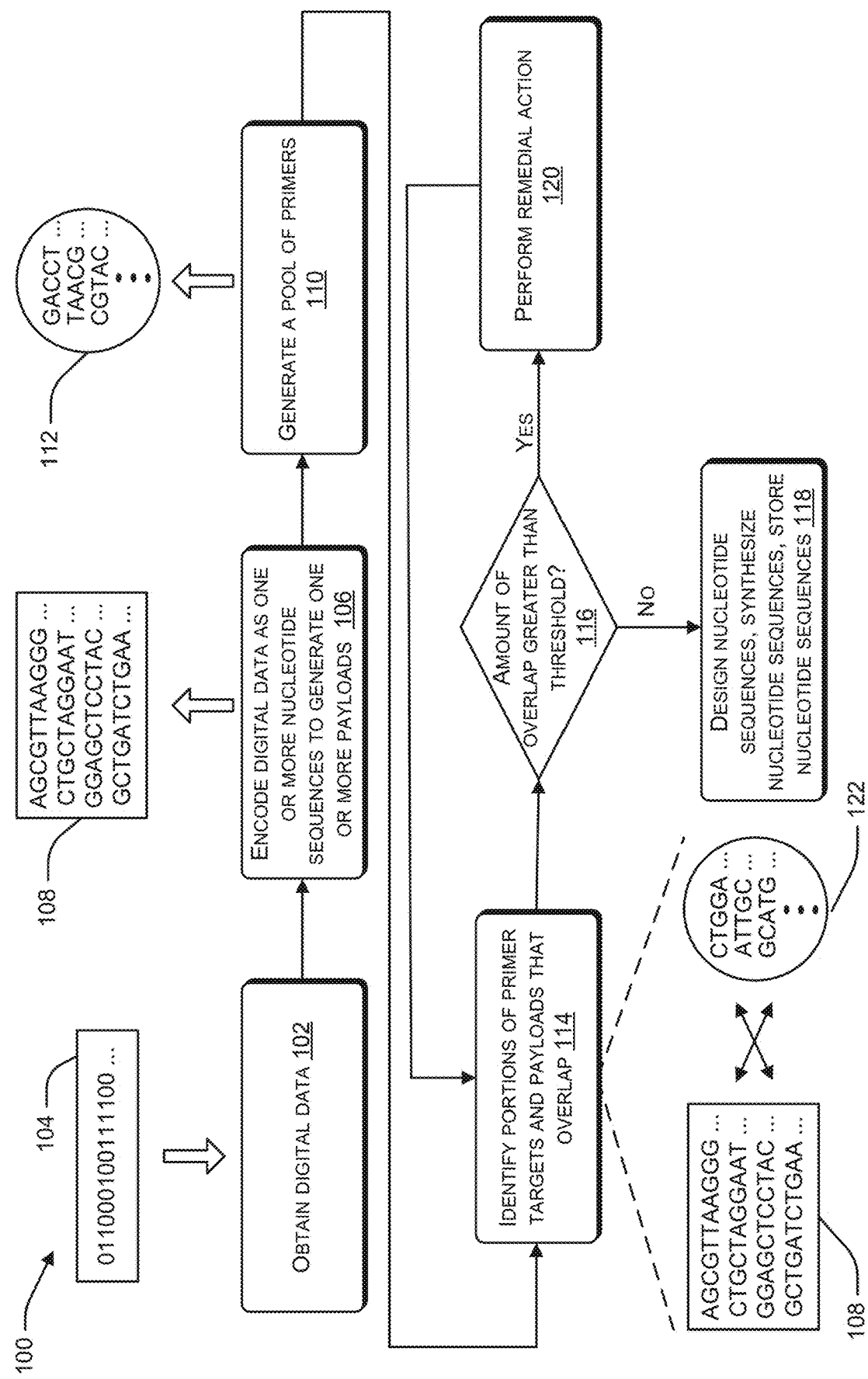
FIG. 1 shows a schematic representation of an example process to produce polynucleotide sequences used to encode digital data. (SEQ ID NOs: 1-4)

This disclosure describes techniques to improve the accuracy of random access of data encoded by polynucleotides and improving the efficiency and specificity of polynucleotide sequence replication and amplification in polynucleotide data storage systems. Much of the data being produced by computing devices is stored on conventional data storage systems that include various kinds of magnetic storage media, optical storage media, and/or solid state storage media. The capacity of conventional data storage systems is not keeping pace with the rates of data being produced by computing devices. Polynucleotide sequences, such as DNA, can be used to store very large amounts of data on a scale that exceeds the capacity of conventional storage systems. An arrangement of nucleotides included in a polynucleotide sequence (e.g., CTGAAGT . . . ) can correspond to an arrangement of bits that encodes data (e.g., 11010001 . . . ). The data can include audio data, video data, image data, text data, software, combinations thereof, and the like.

The polynucleotide sequences can be stored in one or more containers that may also contain a medium, such as a liquid. In particular implementations, polynucleotide sequences can be stored in a liquid, such as water. Each container can store polynucleotide sequences that encode digital data. In response to receiving a request to retrieve particular digital data, one or more polynucleotide sequences can be identified that encode the requested data. A sample can be obtained from a container that includes the polynucleotide sequences corresponding to the requested data. The polynucleotide sequences can be decoded to produce digital data that can be processed by a computing device.

The retrieval of data stored by polynucleotide sequences can be achieved using processes that replicate polynucleotide sequences that are encoding the data that is being requested. For example, polymerase chain reaction (PCR) can be used to replicate polynucleotide sequences that are storing the data being requested. Polynucleotide sequence replication can utilize enzymes, often referred to as "polymerases," that attach to a polynucleotide sequence and produce a complementary strand of that polynucleotide sequence. The polymerases can attach at the primers coupled to the primer targets in the polynucleotide sequences. Polynucleotide replication techniques can be used to produce complementary polynucleotide sequences from a starter polynucleotide sequence to produce thousands of double stranded polynucleotide sequences that correspond to the starter polynucleotide sequence.

In particular implementations, one or more primer targets can be associated with a payload that encodes at least a portion of digital data that is being requested and the payload can be included in a polynucleotide sequence that is stored in a particular container. A primer that includes a sequence of nucleotides that is complementary to the primer target can be added to the container and attach to the primer target. The polymerase using the primer and single stranded target polynucleotide sequences can produce a sufficient number of double stranded polynucleotide sequences from the starter polynucleotide sequence such that sequencing of a sample from the container can produce an output representative of the starter sequence of nucleotides corresponding to the payload. Sequencing can be performed by a device called a sequencer that can provide raw sequence data output referred to herein as reads. Each position in a read is an individual nucleotide determined by the sequencer based on properties of the nucleotides sensed by components of the sequencer. The properties sensed by the sequencer can vary depending on the specific sequencing technology used. The output representing the sequence of nucleotides corresponding to the payload can then be decoded to produce the requested digital data.

Errors can occur in replication of polynucleotide sequences when a nucleotide sequence of a primer target has a threshold amount of overlap with a portion of a payload. Overlap can correspond to a nucleotide in a position in the sequence of nucleotides of the primer target being the same as the same position in a sequence of nucleotides for a portion of a payload. Overlap, as used herein, can also be referred to as sequence identity. To illustrate, a primer target having a sequence of 20 nucleotides, can have an A in a third position, and a sequence of a portion of the payload can also have an A in the third position. In this situation, the primer target and the portion of the payload would overlap in the third position. The amount of overlap between the primer target and the payload corresponds to a number of instances where the same position in the primer target and a portion of the payload has the same nucleotide. If a threshold amount of overlap between a primer target and a payload is present, then during the replication of a polynucleotide sequence that includes the payload, the primer, which is complementary to the primer target, may attach to the portion of the payload that overlaps with the primer target instead of attaching to the primer target itself. Additionally, the binding of primers and polynucleotide sequences of payloads can be predicted based on thermodynamic properties of the sequences of polynucleotides. For example, some thermodynamic properties, such as enthalpy, entropy, and Gibbs free energy, can be used to predict the binding of nucleotide sequences of primers to nucleotide sequences of payloads. In situations where a primer binds to the payload instead of to primer target, a polymerase would start replication from the portion of the payload to which the primer is attached rather than starting replication from the primer target. Consequently, the polynucleotide sequence being replicated can correspond to a portion of the payload and not the entire payload. The replication of the wrong polynucleotide sequence can result in errors when sequencing polynucleotide sequences used to store digital data that is being retrieved.

Also, errors in polynucleotide replication can take place based on certain characteristics of the primers. For example, secondary structure formation caused by the nucleotide sequences of primers can produce errors during a polynucleotide replication process. In another example, primer-dimer formation can produce errors in polynucleotide replication. The melting temperature of primers can also affect the accuracy of polynucleotide replication. Other characteristics of the primers that can affect polynucleotide replication processes can correspond with G/C content of the primers, length of A/T regions of the primers, length of G/C regions of the primers, and differentiation between nucleotide sequences of the primers.

The implementations described herein improve the specificity and efficiency of polynucleotide replication in data retrieval operations by minimizing or eliminating the possibility of nucleotide sequences of primers binding with nucleotide sequences of payloads that encode digital data instead of to a primer target. By minimizing or eliminating the possibility that primers may bind with payloads instead of primer targets, the number of errors that may occur during replication and amplification of nucleotide sequences for the retrieval of data can also be minimized. Additionally, the implementations described herein can utilize primers in polynucleotide sequences that have characteristics that are conducive to the efficient and accurate replication of polynucleotide sequences.

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks can be combined in any order to implement the process, or an alternate process. Moreover, it is also possible that one or more of the provided operations can be modified or omitted.

FIG. 1 shows a schematic representation of an example process 100 to produce polynucleotide sequences used to encode data. At 102, the process 100 can include obtaining digital data 104. The digital data 104 can include a sequence of 1s and 0s that can be processed by a computing device. The digital data 104 can include input and/or output related to one or more applications. In illustrative implementations, the digital data 104 can be related to at least one of audio content, video content, image content, or text content.

At 106, the process 100 can include encoding the digital data 104 as one or more sequences of nucleotides, such as the group of polynucleotide sequences 108. The encoding of the digital data 104 as the group of polynucleotide sequences 108 can be performed according to one or more techniques that associate one or more bits of the digital data 104 with one or more nucleotides. In some implementations, a first group of bits can be associated with a first nucleotide, a second group of bits can be associated with a second nucleotide, a third group of bits can be associated with a third nucleotide, and a fourth group of bits can be associated with a fourth nucleotide. In an illustrative example, a bit pair 00 can correspond to a first nucleotide, such as A; a second bit pair 01 can correspond to a second nucleotide, such as C; a third bit pair 10 can correspond to a third nucleotide, such as G; and a fourth bit pair 11 can correspond to a fourth nucleotide, such as T. In another illustrative example, the binary data 104 can be mapped to a base-4 string with each number in base 4 mapping to a corresponding letter representing a nucleotide. To illustrate, 0, 1, 2, and 3 can each map to one of A, C, G, or T. In an additional illustrative example, the binary data 104 can be mapped to a base-3 string with a nucleotide mapping to each number of the base 3 string (e.g., 0, 1, 2) based on a rotating code. A particular illustrative ternary encoding can be performed according to the following convention:

| | | Previous Nucleotide | | | |
|---|---|---|---|---|---|
| | | A | C | G | T |
| Ternary Digit to Encode | 0 | C | G | T | A |
| | 1 | G | T | A | C |
| | 2 | T | A | C | G |

The process 100 can also include, at 110, generating a group of primers 112. The group of primers 110 can include sequences of nucleotides that include fewer individual nucleotides than the polynucleotides included in the group of polynucleotides 108 used to encode the digital data 104, in some scenarios. In other instances, one or more primers of the group of primers 110 can include a greater number of nucleotides than one or more polynucleotides included in the group of polynucleotide sequences 108. In some implementations, primers included in the group of primers 112 can include at least 3 nucleotides, at least 6 nucleotides, at least 9 nucleotides, at least 12 nucleotides, at least 15 nucleotides, at least 18 nucleotides, at least 21 nucleotides, at least 24 nucleotides, at least 27 nucleotides, or at least 30 nucleotides. Additionally, primers included in the group of primers 112 can include no greater than 100 nucleotides, no greater than 90 nucleotides, no greater than 80 nucleotides, no greater than 60 nucleotides, no greater than 60 nucleotides, no greater than 55 nucleotides, or no greater than 55 nucleotides, no greater than 45 nucleotides, no greater than 42 nucleotides, no greater than 40 nucleotides, no greater than 38 nucleotides, no greater than 35 nucleotides, or no greater than 32 nucleotides. In various implementations, the primers included in the group of primers 112 can be generated by producing pseudo-random arrangements of a number of nucleotides.

Primers can be evaluated against one or more criteria to determine if the primers are to be included in the group of primers 112 and be utilized in polynucleotide sequence replication operations. In some cases, evaluating primers against one or more criteria can include an evaluation of the primers with respect to each other and interactions between the primers that may hinder the amplification and replication of polynucleotides using the primers. The criteria used to evaluate primers can include an amount of G/C content of the primers, a length of regions of the primers including A and T, a length of regions of the primers including G and C, avoidance of secondary structure formed by the primers, melting temperatures of the primers, avoidance of primer-dimer formation, combinations thereof, and the like. The criteria can be used to generate a score for individual primers. In some cases, a score can be generated for each base included in individual primers and the individual base scores can be aggregated. The scores for individual primers can be compared against threshold score and primers having scores below a threshold score can be added to the group of primers 112 and primers having scores above the threshold score can be excluded from the group of primers 112.

Further, at 114, an amount of overlap between nucleotides of the primer targets 122 and nucleotides included in the payloads 108 can be determined. Overlap between nucleotides can indicate a number of nucleotides of a primer target that are the same as a region of a payload. That is, nucleotides in a region of at least one of the payloads 108 and nucleotides of at least one of the primer targets 122 that are the same and are also located in the same position are considered to overlap. For example, an A at position 2 in at least one of the payloads 108 and an A at position 2 in at least one of the primer targets 122 would be identified as overlapping. In this way, each nucleotide of individual primer targets 122 is compared to each nucleotide of the individual payloads 108. Multiple iterations of comparing different regions of consecutive nucleotides of individual payloads 108 with nucleotides of individual primer targets 122 can be performed to determine an overall amount of overlap between individual payloads 108 and individual primer targets 122. Additionally, the operation of 114 can be repeated multiple times for individual primer targets 122 and different payloads 108. In this way, more than one primer target 122 can be identified that may be utilized in conjunction with a respective payload 108. In various implementations, the payloads 108 can be associated with more than one data files and regions of the individual primer targets 122 can be compared with the individual payloads 108 to determine primer targets 122 that can be utilized with respect to payloads 108 of multiple data files.

At 116, the process 100 can determine an amount of overlap between individual primer targets 122 and individual payloads 108 with regard to a threshold. When the amount of overlap between the individual primer targets 122 and the individual payloads 108 is less than a threshold, then the process 100 can proceed to 118, where nucleotide sequences can be designed using the payloads 108 and the primer targets 122, the sequences can be synthesized, and the sequences can be stored for later retrieval using a primer that corresponds with at least one of the primer targets 122 when the information associated with the payloads 108 is requested to be accessed. When the amount of overlap between individual primer targets 122 and individual payloads 108 is greater than the threshold amount, then the process 100 can move to 120 where remedial actions are performed. The remedial actions can reduce the amount of overlap between payloads 108 and primer targets 122. In particular implementations, determining an amount of overlap between individual primer targets 122 and individual payloads 108 with regard to the threshold can include determining a similarity metric between the individual primer targets 122 and the individual payloads 108. In situations where the similarity metric is below a threshold, the process can move to 118, and in situations where the similarity metric is at least a threshold, the process can move to 120.

In particular, at 118, polynucleotide sequences can be designed that include the payloads 108 used to encode the digital data 104 and the primer targets 122 that correspond to primers from the group of primers 112. A polynucleotide sequence can include an individual payload 108 and one or more primers from the group of primers 112. In some implementations, the one or more primers 112 associated with each payload 108 can be assigned to the individual payload 108 in an arbitrary manner. In illustrative implementations, a polynucleotide sequence can include a payload and two primer targets that correspond to one or more primers from the pool of primers 112. Each of the primer targets associated with the individual payload 108 can include a different sequence of nucleotides. In some implementations, the polynucleotide sequence can include a first primer target on a first end of the polynucleotide sequence and a second primer target on a second end of the polynucleotide sequence. For example, the polynucleotide sequence can include a first primer target on a 3' end and a second primer target on a 5' end. The primer targets can be used as endpoints in marking the beginning point of the polynucleotide replication process and an endpoint of the polynucleotide replication process. The primer target on the 3' end can be used for replication in a forward direction and the primer target on the 5' end can be used for replication in a reverse direction.

The polynucleotide sequences assembled at 118 can also include regions of one or more nucleotides that encode other information. For example, a polynucleotide sequence can include information used in the retrieval of the binary data 104. In some implementations, the digital data 104 can be divided into multiple strings with each string being encoded by a payload 108 of a corresponding polynucleotide sequence. Addressing information can be used to identify the different polynucleotide sequences that include the payloads 108 encoding the digital data 104. The addressing information can also indicate an order in which the polynucleotides sequences are to be decoded to reconstruct the bits included in the digital data 104. The polynucleotide sequences assembled at 118 can also include one or more regions that correspond to additional information, such as error correction information. Additionally, in some examples, the primer targets 122 can encode information, such as addressing information and/or a key that is used in the retrieval of the digital data 104 using polynucleotide sequences.

In particular implementations, additional information included in polynucleotide sequences, such as addressing information and/or error correction information, can also be compared to the primer targets 122 to determine an amount of overlap between the primer targets 122 and the additional information. The additional information can be included in one or more metadata regions of the polynucleotide sequences. In some situations, the nucleotides related to the additional information can be compared with nucleotides of individual primer targets 122 to determine an amount of overlap between the nucleotides encoding the additional information and the nucleotides of the individual primer targets 122. For example, an amount of overlap can be determined between a metadata region of a polynucleotide and a primer target 122. In various implementations, if the amount of overlap between one or more of the primer targets 122 and the nucleotides related to the additional information is greater than a threshold, then the nucleotides of the one or more primer targets 122 and/or the nucleotides of the additional information can be modified to decrease the amount of overlap between the one or more primer targets 122 and the nucleotides related to the additional information. Also, an amount of overlap can be determined between a metadata region and individual payloads 108. In scenarios where an amount of overlap between a metadata region of a polynucleotide sequence and individual payloads 108 is greater than a threshold, then the nucleotides of the individual payloads 108 and/or the nucleotides of the metadata region can be modified to decrease the amount of overlap.

Designing the polynucleotide sequences can include generating a metadata storage component, such as a data table that indicates the primer targets associated with each payload and/or other information associated with each payload. For example, a data storage structure can indicate a payload and digital data that is being encoded by the payload. Also, the data storage structure can indicate one or more primer targets included in a polynucleotide sequence that includes the payload. Additionally, the data storage structure can indicate addressing information and/or a key included in a polynucleotide sequence that corresponds to the payload.

After the polynucleotide sequences are designed, the polynucleotide sequences can be synthesized and stored. The synthesis of polynucleotide sequences can be performed using automated oligonucleotide synthesis techniques such as, for example, those employed by companies such as Integrated DNA Technologies (IDT®), GenScript® and BioAutomation. After synthesizing the polynucleotide sequences, the polynucleotide sequences can be stored in a medium. In some implementations, data from a number of digital files can be encoded by a number of polynucleotide sequences that are stored in one or more pools of liquid. The data encoded by the polynucleotide sequences can be retrieved by obtaining a sample from one or more pools that store the polynucleotide sequences, amplifying the target polynucleotide sequences using polynucleotide replication techniques, and then sequencing the sample. The amplification process can produce an amplification product that includes many copies of the target polynucleotide sequences. The term "amplify", can refer to an "exponential" increase in the number of copies of the target polynucleotide sequence and can be used to describe both linear and exponential increases in the numbers of a select polynucleotide sequence.

At 120, remedial action can be performed based on a determination that an amount of overlap between a nucleotide sequence of at least one primer target and a nucleotide sequence of a payload is greater than a threshold amount. In other cases, remedial actions can be triggered in response to one or more formulas applied to the amount of overlap between the individual payloads 108 and the individual primer targets 122 with respect to a threshold amount of overlap. For example, an average or mean of the amounts of overlap between individual payloads 108 and the individual primer targets 122 and a standard deviation and can be compared to a threshold amount of overlap. In these situations, the threshold amount of overlap can be related to an aggregate amount of overlap for all of the payloads 108 and all of the primer targets 122. A remedial action can be performed based at least partly on the aggregate overlap between the payloads 108 and the primer targets 122 being greater than the aggregate threshold overlap or based at least partly on the aggregate overlap between the payloads 108 and the primer targets 122 being within one or more standard deviations of the aggregate threshold overlap. The remedial action can include comparing a nucleotide sequence of a different, alternate primer target with the nucleotide sequence of the payload. In these scenarios, the process 100 can return to 114 and the nucleotide sequence of the different primer target can be compared with the nucleotide sequence of the payload to determine an amount of overlap between the different primer target and the payload. The remedial action can also include modifying one or more nucleotides of the primer target to reduce the amount of overlap between the payload and the primer target.

In some implementations, a remedial action performed at 120 can include randomizing the digital data 104. For example, a randomizing algorithm can be applied to the digital data 104 to produce randomized digital data. In various implementations, the randomized digital data can be produced by generating a string of numbers (e.g., a string of binary digits) using the randomization algorithm and performing an XOR operation between the digital data 104 and the string of numbers. The randomized digital data can then be re-encoded and the new alternate nucleotide sequences of the payloads encoding the randomized digital data can be different from the previous nucleotide sequences used to encode the digital data 104. In these situations, the process 100 can return to 114 and the new, alternate nucleotide sequences for the payloads encoding the randomized digital data can then be compared with one or more primer targets 122 corresponding to the primers of the pool of primers 112 to determine an amount of overlap. In various implementations, the digital data 104 can be randomized multiple times before the amount of overlap between the new, alternate nucleotide sequences of the payloads and the nucleotide sequences of the primer targets is less than the threshold amount. In various implementations, the string of bits used to produce the randomized digital data can be stored in a data structure that is accessible to a computing device performing the randomization. In particular implementations, the string of bits can be encoded by one or more nucleotides in the metadata of polynucleotide sequences produced according to the process 100. The sequences used to encode the string of bits used in the randomization process, either individually or in combination with other nucleotides of the metadata, can have less than a threshold amount of overlap with regions of the payloads 108.

Figure 2:
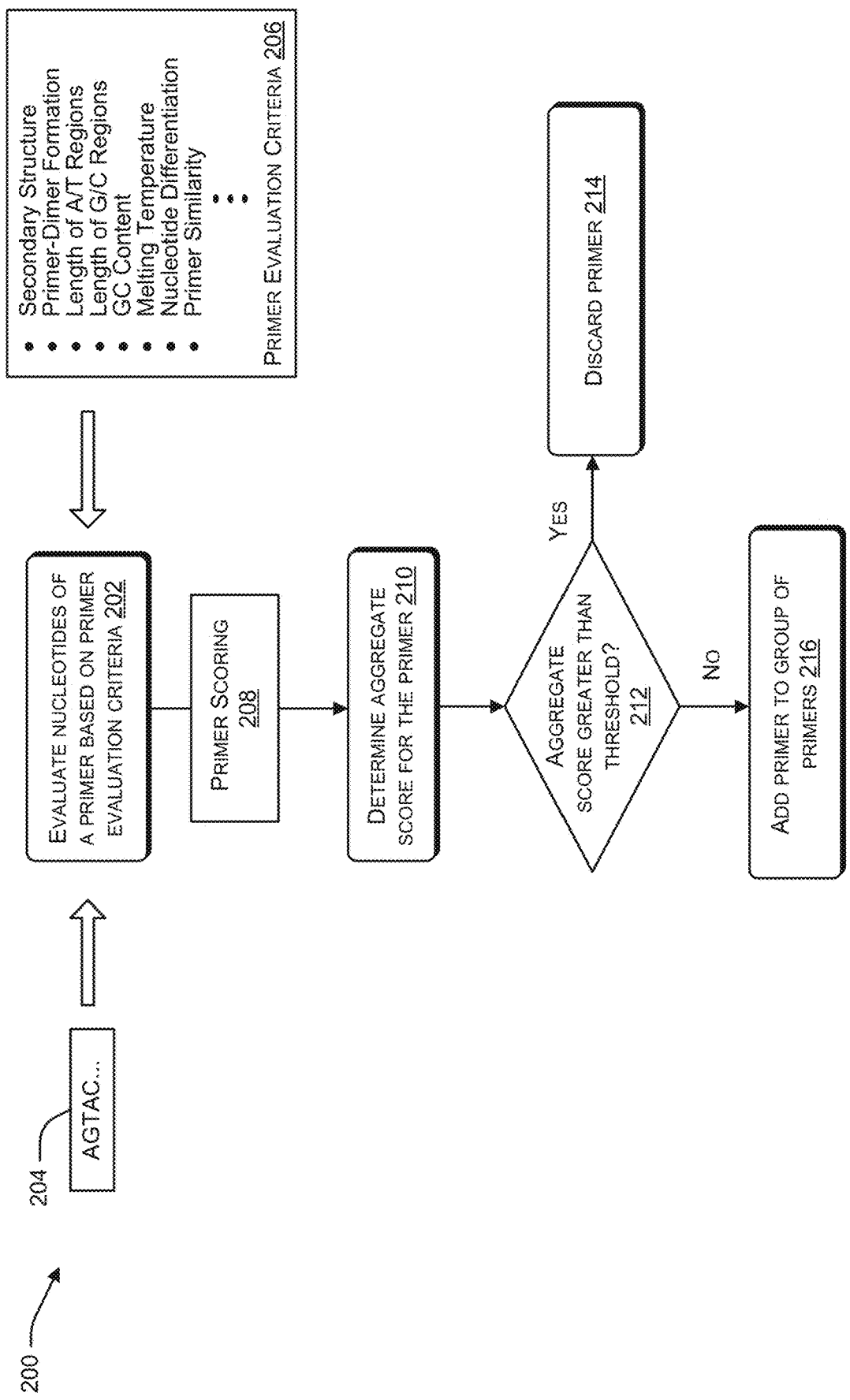
FIG. 2 shows a schematic representation of an example process to produce a group of primers used to retrieve digital data encoded by polynucleotide sequences.

FIG. 2 shows a schematic representation of an example process 200 to produce a group of primers used to selectively amplify polynucleotide sequences. At 202, nucleotides of a primer 204 are evaluated based on one or more primer evaluation criteria 206. In some implementations, each nucleotide of the primer 204 is evaluated according to the primer evaluation criteria 206. Additionally, the primer 204 can be evaluated as a whole according to the primer evaluation criteria 206 or one or more groups of nucleotides of the primer 204 can be evaluated according to the primer evaluation criteria 206.

The primer evaluation criteria 206 can include formation of secondary structure by the primer 204. In some cases, arrangements of nucleotides can form secondary structures, such as loop structures or knot structures. The formation of secondary structure can take place based on interactions between the nucleotides of the primer 204 that cause the nucleotides to be attracted to each other. When nucleotides of the primer 204 are attracted to each other, the linear arrangement of nucleotides of the primer 204 can be disrupted. Secondary structures can sometimes be formed based on interactions between complementary nucleotides of a primer. The formation of secondary structures by primers can inhibit the binding of the primer to a polynucleotide sequence thereby inhibiting the replication of that polynucleotide sequence.

The primer evaluation criteria 206 can also include primer-dimer formation. Primer-dimer formation can take place during polynucleotide replication when nucleotides at an end of two primers are complementary and become attached. Primer-dimer formation can take place at the 3' ends of primers in some scenarios. The formation of primer-dimers during a nucleotide replication process can reduce the number of unbound primers available for use in replication of the polynucleotide sequences. Thus, errors can occur in the sequencing of polynucleotides that are amplified by primers that can form primer-dimers. By evaluating primers before associating them with respective payloads, the errors in polynucleotide replication can be minimized.

In addition, the primer evaluation criteria 206 can include evaluating the length of A/T regions of the primer 204 and the length of G/C regions of the primer 204. The length of A/T regions of the primer and the length of G/C regions of the primer 204 can affect temperature at which a primer separates from a complementary single-stranded polynucleotide (the "melting temperature") which in turn can affect the accuracy of polynucleotide replication. Increased G/C content increases the melting temperature, while conversely increased A/T content decreases the melting temperature. In particular, the amount of energy used to break the bonds between G's and C's is greater than the energy used to break the bonds between A's and T's. Thus, the greater the G/C content in a polynucleotide, the greater the melting temperature of the polynucleotide.

Further, the primer evaluation criteria 206 can include G/C content. In some implementations, G/C content of primers included in a pool of primers can be at least 38%, at least 40%, at least 42%, at least 45%, at least 48%, or at least 50%. Also, G/C content of primers included in a pool of primers can be no greater than 62%, no greater than 60%, no greater than 58%, no greater than 55%, or no greater than 52%. In illustrative examples, the G/C content of primers included in a pool of primers can be from 38% to 62%. In other illustrative examples, the G/C content of primers included in a pool of primers can be from 42% to 58%. In additional illustrative examples, the G/C content of primers included in a pool of primers can be from 45% to 55%. In a particular illustrative example, the G/C content of primers included in a pool of primers can be about 50%, while A/T content of primers included in a pool of primers can be about 50%.

The primer evaluation criteria 206 can include melting temperature. Melting Temperature ($T_m$) can refer to the temperature at which one half of a DNA duplex will dissociate to become single stranded and indicates the duplex stability. In particular implementations, primers can be evaluated based on whether the melting temperature is from 52° C. to 62° C. Additionally, primers can be evaluated based on whether the melting temperature is form 53° C. to 61° C. Further, primers can be evaluated based on whether the melting temperature is from 55° C. to 60° C.

Additionally, the primer evaluation criteria 206 can include nucleotide differentiation. Nucleotide differentiation refers to differences between any two nucleotides of a primer. An amount of nucleotide differentiation for the primer 204 can be determined by comparing each of the nucleotides included in the primer 204 with each of the other nucleotides included in the primer 204. The amount of nucleotide differentiation can be expressed as a percentage of the nucleotides of the primer 204 that are different from one another. In some implementations, an amount of nucleotide differentiation for primers to be included in a pool of primers for assembling polynucleotides can be at least 20%, at least 22%, at least 25%, at least 28%, at least 30%, at least 32%, or at least 35%. In an illustrative implementation, an amount of nucleotide differentiation for primers to be included in a pool of primers for assembling polynucleotides can be at least 30%.

The primer evaluation criteria 206 can include primer similarity. Primer similarity can correspond to a number of nucleotides of one primer that are the same as the nucleotides of another primer. In some cases, the primer similarity relates to the similarities between two sequences of nucleotides that are considered for use as a primer regardless of the ordering of the nucleotides in the different sequences. That is, similarity between two sequences can be based at least partly on a number of A's in the two sequences, a number of G's in the two sequences, a number of T's in the two sequences, and a number of C's in the two sequences. In some instances, a sequence alignment algorithm can be used to determine similarities of nucleotide sequences. In an illustrative example, a Basic Local Alignment Search Tool (BLAST) can be used to determine an amount of similarity between nucleotide sequences. In particular implementations, an amount of similarity between nucleotides included in a pool of primers used in polynucleotide sequences that encode digital data can be no greater than 60%, no greater than 55%, no greater than 50%, no greater than 45%, no greater than 40%, or no greater than 35%.

Evaluating the primer 204 based on the primer evaluation criteria 206 can generate primer scoring 208. The primer scoring 208 can include multiple scores for the primer 204. In some cases, the scores included in the primer scoring 208 can correspond to each of the nucleotides included in the primer 204. For example, the primer scoring 208 can correspond to an evaluation of each nucleotide of the primer 204 with respect to each of the primer evaluation criteria 206. To illustrate, a first nucleotide of the primer 204 can be evaluated according to the secondary structure criteria to generate a first score. The first nucleotide of the primer 204 can then be evaluated according to the primer-dimer formation criteria and a second score can be produced. The scores included in the primer scoring 208 can be numerical, such as +1, 0, −1. The scores included in the primer scoring 208 can also be arranged according to a scale, such as a scale from 1 to 10.

The scores generated in association with the primer scoring 208 can provide an indication of the deviation of a nucleotide or the primer 204 as a whole from an ideal case. In various implementations, the ideal case for a nucleotide or sequence of nucleotides can be defined according to metrics for each of the primer evaluation criteria 206 that correspond to the least number of errors in polynucleotide amplification. For example, an ideal case for a primer can correspond to a specified range of melting temperatures, a threshold probability of forming secondary structure, a threshold probability of primer-dimer formation, a maximum length of A/T regions, a maximum length of G/C regions, a range of G/C content, a particular amount of nucleotide differentiation, a threshold amount of nucleotide similarity, or combinations thereof.

In an illustrative implementation, a first score can be generated for a nucleotide when the nucleotide participates in causing the primer 204 to have a secondary structure, while a second score can be generated when the nucleotide does not cause the primer 204 to have a secondary structure. In some cases, the primer scoring 208 can be based at least partly on a probability that the primer 204 will produce secondary structure. In various implementations, a determination that a probability that the primer 204 will produce secondary structure that is at least a threshold probability can cause a first score to be assigned to the sequence of nucleotides of the primer 204, while a probability that the primer 204 will produce secondary structure that is less than a threshold probability can cause a second, different score to be assigned to the sequence of nucleotides of the primer 204.

In another illustrative implementation, a nucleotide of the primer 204 can receive a particular score based on a prediction that the nucleotide may participate in the formation of a dimer with another primer. In some implementations, a nucleotide can receive a first score based on a first probability that the nucleotide would participate in primer-dimer formation and a second, different score based on a second probability that the nucleotide would participate in primer-dimer formation. For example, a threshold probability that a nucleotide would participate in primer-dimer formation can be specified and a nucleotide having a probability of participating in primer-dimer formation satisfying the threshold probability would be assigned a first score and a nucleotide having a probability of participating in primer-dimer formation that does not satisfy the threshold probability would be assigned a second, different score. In other examples, a scale can designate scores for various ranges of probabilities of a nucleotide participating in primer-dimer formation. To illustrate, a first nucleotide having a first probability of participating in primer-dimer formation that is within a first range (e.g., 0% to 10%) can be assigned a first score, a second nucleotide having a second probability of participating in primer-dimer formation that is within a second range (e.g., 11% to 30%) can be assigned a second score, and a third nucleotide having a third probability of participating in primer-dimer formation that is within a third range (e.g., above 30%) can be assigned a third score.

In addition, a nucleotide can be assigned a score based on being included in an A/T region of a certain length. For example, a first nucleotide included in an A/T region having a first length can be assigned a first score and a second nucleotide included in an A/T region having a second length can be assigned a second, different score. Each nucleotide included in an A/T region of a particular length can be assigned the same score. In various implementations, a threshold length for A/T regions can be designated and a nucleotide included in an A/T region that meets or exceeds the threshold length can be assigned a first score, while another nucleotide included in an A/T region that is less than the threshold length can be assigned a second, different score. In some cases, multiple ranges of lengths of A/T regions can be associated with different scores that can be assigned to nucleotides included in an A/T region of the primer 204 based on the range that the length of the A/T region of the primer 204 falls within.

Also, a nucleotide can be assigned a score based on included in a G/C region of a certain length. For example, a first nucleotide included in a G/C region having a first length can be assigned a first score and a second nucleotide included in a G/C region having a second length can be assigned a second, different score. Each nucleotide included in a G/C region of a particular length can be assigned the same score. In various implementations, a threshold length for G/C regions can be designated and a nucleotide included in a G/C region that meets or exceeds the threshold length can be assigned a first score, while another nucleotide in an G/C region that is less than the threshold length can be assigned a second score. In some cases, multiple ranges of lengths of G/C regions can be associated with different scores that can be assigned to nucleotides included in a G/C region of the primer 204 based on the range that the length of the G/C region of the primer 204 falls within.

Further, a nucleotide can be assigned a score based on G/C content of the primer 204. In some implementations, each G or C of the primer 204 can be assigned a score based on the overall G/C content of the primer 204. For example, based on the primer 204 having G/C content that is included in a particular range (e.g., 45% to 55%), each G and C of the primer 204 can be assigned a score that is associated with the particular range. Additionally, in situations where the G/C content of the primer 204 is outside of the particular range, each G and C of the primer 204 can be assigned another score that is associated with G/C content outside of the particular range. In some cases, multiple ranges of G/C content can be associated with different scores that can be assigned to nucleotides of the primer 204 based on the range that the G/C content of the primer 204 falls within.

A nucleotide of the primer 204 can be assigned a score based on a melting temperature of the primer 204. In illustrative implementations, the score assigned to each nucleotide of the primer 204 can be based on the melting temperature of the primer 204 being included in a range of melting temperatures. In some implementations, nucleotides of the primer 204 can be assigned a first score based on the melting temperature of the primer 204 being in a first range of melting temperatures and the nucleotides of the primer 204 can be assigned a second, different score if the melting temperature of the primer 204 is included in a second range of melting temperatures. A score can be assigned to nucleotides of the primer 204 based on a melting temperature threshold. To illustrate, the nucleotides of the primer 204 can be assigned a first score when the melting temperature of the primer 204 is below a threshold melting temperature and the nucleotides of the primer 204 can be assigned a second, different score when the melting temperature of the primer 204 meets or exceeds the threshold melting temperature. In some cases, multiple ranges of melting temperatures can be associated with different scores that can be assigned to nucleotides included in the primer 204 based on the range that the melting temperature of the primer 204 falls within.

Nucleotides of the primer 204 can be assigned a score based on an amount of differentiation between the nucleotides of the primer 204. In various implementations, each nucleotide can be assigned a score based on the amount of differentiation between the nucleotides of the primer 204 being less than a threshold amount of differentiation. The nucleotides of the primer 204 can be assigned another score when the amount of differentiation between nucleotides of the primer 204 meet or exceed a threshold amount of differentiation. In some examples, the amount of nucleotide differentiation for a primer can be divided into a number of ranges and a score for the nucleotides of the primer 204 with respect to nucleotide differentiation can be determined based on the range in which the amount of nucleotide differentiation falls.

Nucleotides of the primer 204 can be assigned a score based on an amount of similarity between the sequence of the nucleotides of the primer 204 and the sequences of nucleotides of other primers. For example, nucleotides of the primer 204 can be assigned a first score when an amount of similarity between the primer 204 and one or more additional primers meets or exceeds a threshold similarity and nucleotides of the primer 204 can be assigned a second, different score when an amount of similarity between the primer 204 and one or more additional primers is less than a threshold similarity. In some instances, the similarity between primers can be divided into a number of ranges and a score for nucleotides of the primer 204 with respect to sequence similarity between the primer 204 and the one or more additional primers can be determined based on the range in which the sequence similarity falls.

In other situations, the primer scoring 208 can correspond to a respective score for the primer 204 according to each of the primer evaluation criteria 206. In this way, the primer 204 can have a first score for a first primer evaluation criteria 206, such as secondary structure, a second score with respect to a second primer evaluation criteria 206, such as primer-dimer formation, and so forth.

At 210, the process 200 includes utilizing the nucleotide and/or primer scoring 208 to determine an aggregate score for the primer 204. In some implementations, a score can be determined for each nucleotide of the primer 204 for each of the primer evaluation criteria 206. In these situations, the aggregate score for the primer 204 can be determined by combining the scores for each nucleotide of the primer 204 for each of the primer evaluation criteria 206 for the primer 204. In additional implementations, a score can be determined for the primer 204 as a whole for each of the primer evaluation criteria 206. In these scenarios, the aggregate score for the primer 204 can be determined by combining the scores for each of the primer evaluation criteria 206 for the primer 204.

At 212, the process 200 includes determining whether the aggregate score is greater than a threshold score. In some instances, the threshold score can be determined based on a probability that a given primer may cause errors in polynucleotide replication processes. In situations where the aggregate score for the primer 204 is greater than a threshold, the process 200 can move to 214 where the primer 204 is discarded and not included in a group of primers to be utilized in data storage and retrieval operations using polynucleotide sequences. In instances where the aggregate score for the primer 204 is less than or equal to the threshold score, the process 200 can proceed to 216 and the primer 204 can be added to a group of primers used in data storage and retrieval operations using polynucleotide sequences.

FIG. 3 shows a table 300 that includes example scoring for nucleotides included in a primer according to a number of primer evaluation criteria. The table 300 shows scoring for nucleotides 302, 304, 306 in different positions of a primer 308 with respect to a number of different primer evaluation criteria 310, 312, 314, 316, 318, 320, 322. In particular, the table 300 can include a number of scores for each of the nucleotides of the primer 308. For example, the first nucleotide 302 can have a score of 0 for the first primer evaluation criteria 310, the second primer evaluation criteria 312, the third primer evaluation criteria 314, the fourth primer evaluation criteria 316, the fifth primer evaluation criteria 318, the sixth primer evaluation criteria 320, and the seventh primer evaluation criteria 322. The table 300 also indicates that the second nucleotide 304 of the primer 308 can have a score of 0 for the primer evaluation criteria 310, 312, 314, 322 and a score of 1 for the primer evaluation criteria 316, 318, 320. Further, the table 300 indicates that the third nucleotide 306 of the primer 308 can have a score of 0 for the primer evaluation criteria 312, 314, 316, and 322 and a score of 1 for the primer evaluation criteria 310, 320, and 322.

Figure 4:
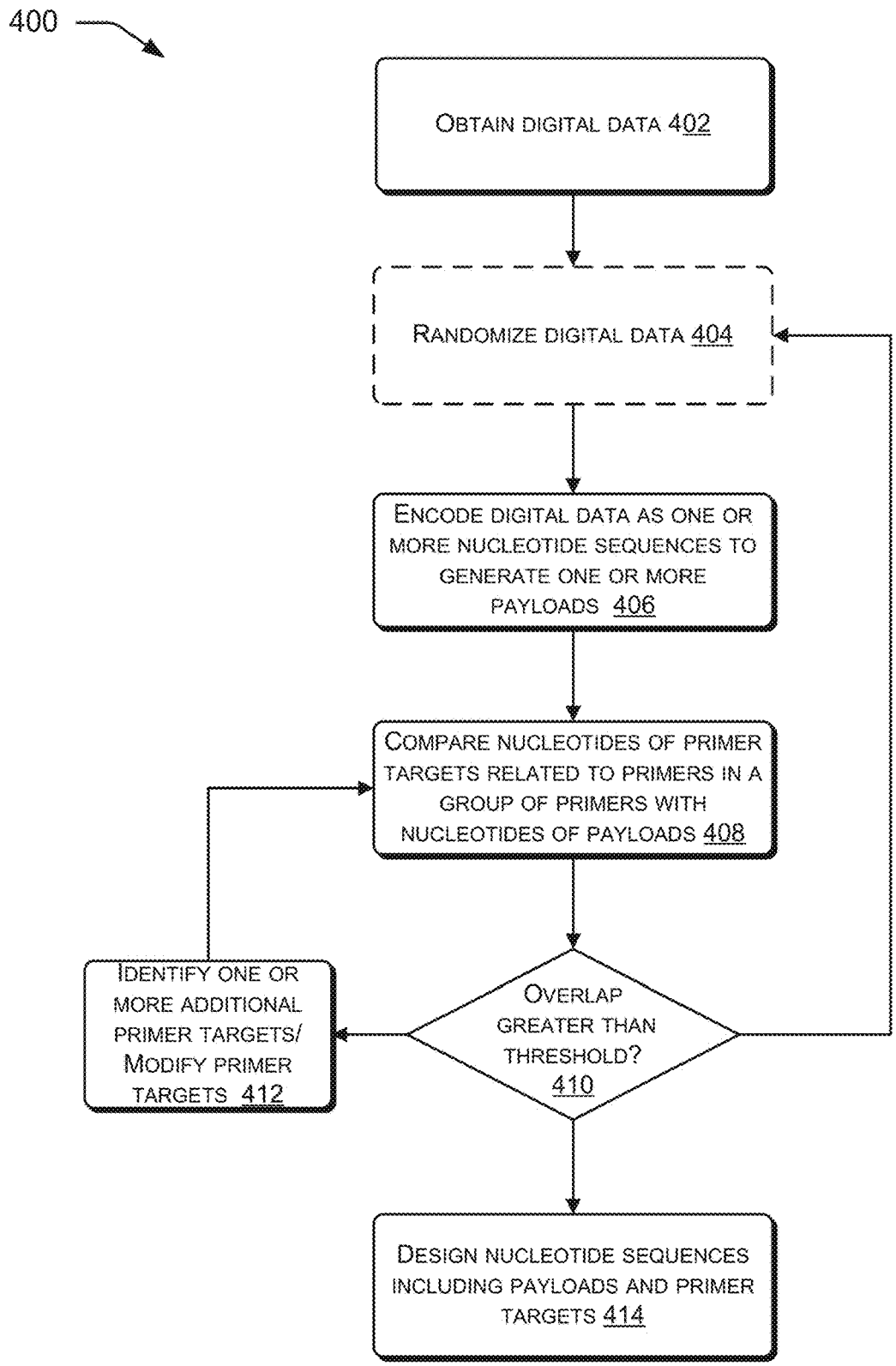
FIG. 4 shows a flow diagram of an example process to produce polynucleotide sequences having a payload encoding digital data that includes a minimum amount of overlap with one or more primer target regions of the polynucleotide sequence.

FIG. 4 shows a flow diagram of an example process 400 to produce polynucleotide sequences having a payload encoding digital data that includes a minimum amount of overlap with one or more primer regions of the polynucleotide sequence. At 402, the process 400 includes obtaining digital data. The digital data can include a string of bits. In some cases, the digital data can include image data, audio data, video data, text data, or combinations thereof. In various implementations, the digital data can be stored in one or more data files.

Optionally, the process 400 includes, at 404, randomizing the digital data. Randomizing the digital data can include applying one or more pseudo-random number generation algorithms to the digital data. Randomizing the digital data modifies the order of the bits included in the digital data. The data can be randomized, in some implementations, by generating a string of numbers using a pseudo-random number generation algorithm and performing an XOR operation between the string of numbers and the digital data. In some implementations, randomizing the digital data can include randomizing addressing information or other information that is included in the payload, as well as the digital data itself.

At 406, the process 400 includes encoding the digital data as one or more nucleotide sequences to generate one or more payloads that correspond to the digital data. Encoding the digital data can include assigning one or more nucleotides to one or more bits of the digital data. In some implementations, a single nucleotide, such as A, G, C, or T, can be used to encode a 1 or 0 of the digital data. In particular implementations, the digital data can be encoded according to a base-2 sequence of nucleotides. Additionally, the digital data can be encoded according to a base-3 sequence of nucleotides. The digital data can also be encoded according to a base-4 sequence of nucleotides. In some scenarios, the length of the string of bits of the digital data can be segmented and individual segments can be encoded as a sequence of nucleotides. In particular examples, the length of the payloads of polynucleotides encoding digital data can be limited due to polynucleotides beyond a threshold length producing errors during polynucleotide replication. In these situations, the bit string encoding the digital data can be divided into segments of bits that can be encoded with sequences of nucleotides having a length that is no greater than the threshold length.

In illustrative implementations, the digital data can be encoded to avoid homopolymers in a payload. Homopolymers are repetitions of a nucleotide at adjacent positions in a sequence of nucleotides. In some cases, the digital data can be encoded to exclude homopolymers by using a base-3 encoding. In particular implementations, a base-3 encoding can encode a ternary bit (e.g., 0, 1, or 2) as a nucleotide based on the previous nucleotide in the sequence that encoded the previous bit. For example, a rotating code can be used to encode a ternary bit of digital data as a nucleotide. To illustrate, a 0 can be encoded as C when preceded by A, G when preceded by C, T when preceded by G, and A when preceded by T. Additionally, 1 can be encoded as G when preceded by A, T when preceded by C, A when preceded by G, and C when preceded by T. Further, 2 can be encoded as T when preceded by A, A when preceded by C, C when preceded by G, and G when preceded by T.

At 408, the process 400 can include comparing nucleotides of primer targets with nucleotides of payloads. The nucleotides of the primer targets can be compared to the nucleotides of the payloads to determine an amount of overlap between the nucleotides of the primer targets and the nucleotides of the payloads. The amount of overlap between the nucleotides of the primer targets and the nucleotides of the payloads can indicate a number of nucleotides of the primer target that are the same as nucleotides of the payload at corresponding positions. In illustrative implementations, the amount of overlap between the nucleotides of the primer targets and the nucleotides of the payload can be determined by determining an amount of sequence identity between the primer target sequences and the payload sequences using a Basic Local Alignment Search Tool (BLAST). The fewer the number of nucleotides of the primer targets that are the same as nucleotides of a payload, the lower the probability that primers corresponding to the primer targets will bind to the payload instead of the primer targets.

In various implementations, a number of nucleotides of the primer targets can be less than the number of nucleotides in the payloads. In these scenarios, portions of the nucleotides of the payload can be compared to the nucleotides of the primer targets. In particular implementations, a first portion of the nucleotides of a payload can be compared with nucleotides of a primer target at corresponding positions. Subsequently, a second portion of the nucleotides of the payload can be compared with the nucleotides of the primer target at corresponding positions where the second portion of the nucleotides of the payload include different nucleotides than the first portion.

In some implementations, an initial comparison between the nucleotides of a payload and the nucleotides of a primer target can start with a first number of nucleotides of the payload being compared with a first number of nucleotides of the primer target at corresponding positions. For example, a primer target can have 25 nucleotides, and an initial comparison between the nucleotides of the primer target and the nucleotides of the payload can include comparing the first 25 nucleotides of the payload with the 25 nucleotides of the primer target. In this example, the first nucleotide of the payload is compared with the first nucleotide of the primer target, the second nucleotide of the payload is compared with the second nucleotide of the primer target, the third nucleotide of the payload of the payload is compared with the third nucleotide of the primer target and so forth until the 25th nucleotide of the payload is compared with the 25th nucleotide of the primer target. In various implementations, the comparison can continue in a sliding manner such that the 25 nucleotides of the primer target can be compared to 25 nucleotides of the payload, but starting at a second nucleotide of the payload instead of the first nucleotide. To illustrate, the second nucleotide of the payload can be compared to the first nucleotide of the primer target, the third nucleotide of the payload can be compared to the second nucleotide of the primer target, the fourth nucleotide of the payload can be compared to the third nucleotide of the primer target and so forth until the 26th nucleotide of the payload is compared with the 25th nucleotide of the primer target. Subsequent comparisons between the nucleotides of the payload and the nucleotides of the primer target can continue until the final 25 nucleotides of the payload are compared with the 25 nucleotides of the primer.

At 410, the process 400 includes determining whether an amount of overlap between the nucleotides of the payload and the nucleotides of the primer target is greater than a threshold amount of overlap. The threshold amount of overlap can correspond to a probability that a primer used in polynucleotide sequence replication would interact with the payload of a polynucleotide instead of interacting with a primer target of the polynucleotide, which can result in errors in the replication of the polynucleotide sequence. In illustrative implementations, the probability that a primer used in polynucleotide sequence replication can bind to a payload instead of a primer target can correspond to a number of nucleotides of a primer target that overlap with one or more regions of the nucleotides of a payload. For example, a first probability that a primer used in polynucleotide sequence replication would interact with a payload can correspond to a first number of nucleotides of a corresponding primer target overlapping with nucleotides of one or more regions of a payload. In addition, a second probability that a primer used in polynucleotide sequence replication would interact with a payload can correspond to a second number of nucleotides of a corresponding primer target overlapping with nucleotides of one or more regions of a payload. In a first illustration, when 8 nucleotides of a 25-nucleotide primer target are the same as 8 nucleotides in corresponding positions of a 25-nucleotide sequence of a payload, a first probability, such as 40%, that a primer utilized in polynucleotide sequence replication would interact with the payload instead of the primer target can be calculated. In a second illustration, when 4 nucleotides of a 25-nucleotide primer target are the same as 4 nucleotides in corresponding positions of a 25-nucleotide sequence of a payload, a second probability, such as 15%, that a primer utilized in polynucleotide sequence replication would interact with the payload instead of the primer target can be calculated. In scenarios where a probability of 20% that a primer used in polynucleotide sequence replication would interact with a payload instead of a primer target corresponds to a threshold amount of overlap, the first illustration described above would result in a determination that the amount of overlap between the primer target and the payload is greater than the threshold and the second illustration described above would result in a determination that the amount of overlap between the primer target and the payload is less than the threshold.

In cases where the amount of overlap is greater than the threshold amount of overlap, the process 400 can return to 404 or the process 400 can move to 412. In situations where the process 400 returns to 404, the digital data can be randomized or re-randomized to create a different string of bits to be encoded than a previously encoded sting of bits. By modifying a previous string of bits through one or more pseudo-random number algorithms, an alternate sequence of nucleotides encoding the new string of bits can have a different amount of overlap with the primer target. In some implementation, the amount of overlap between the primer target and the new encoding of the payload can be less than the threshold amount of overlap. In situations where the process moves to 412, where an alternate primer target can be identified, the process 400 can return to 408 to compare the nucleotide sequences of the alternate primer target to the payload. In other cases, at 412, one or more nucleotides of the primer target can be modified and the process 400 can return to 408 to compare the new nucleotide sequence of the primer target with the payload.

In cases where the amount of overlap is less than the threshold amount of overlap, the process 400 moves from 410 to 414. At 414, a polynucleotide sequence can be generated that includes the payload and the primer target. Additionally, a primer can be generated that is the complement of the primer target. In some implementations, the polynucleotide sequence can also include another primer target that has less than the threshold amount of overlap with the payload. One of the primer targets can be located on the 3' end of the polynucleotide sequence and the other primer target can be located on the 5' end of the polynucleotide sequence. The polynucleotide sequence can also include other nucleotides that correspond to additional information. For example, the polynucleotide sequence can also include addressing information to be used in identifying a digital file associated with the digital bits encoded by the polynucleotide sequence. The addressing information can indicate the position of the digital bits encoded by the polynucleotide sequence within the larger bit stream of the digital file. In various implementations, at least a portion of the addressing information can be encoded by one or more nucleotides of the primer target. In additional implementations, the polynucleotide sequence can include error correction information. After generating the polynucleotide sequence, the polynucleotide sequence can be synthesized and stored in a polynucleotide storage medium.

Figure 5:
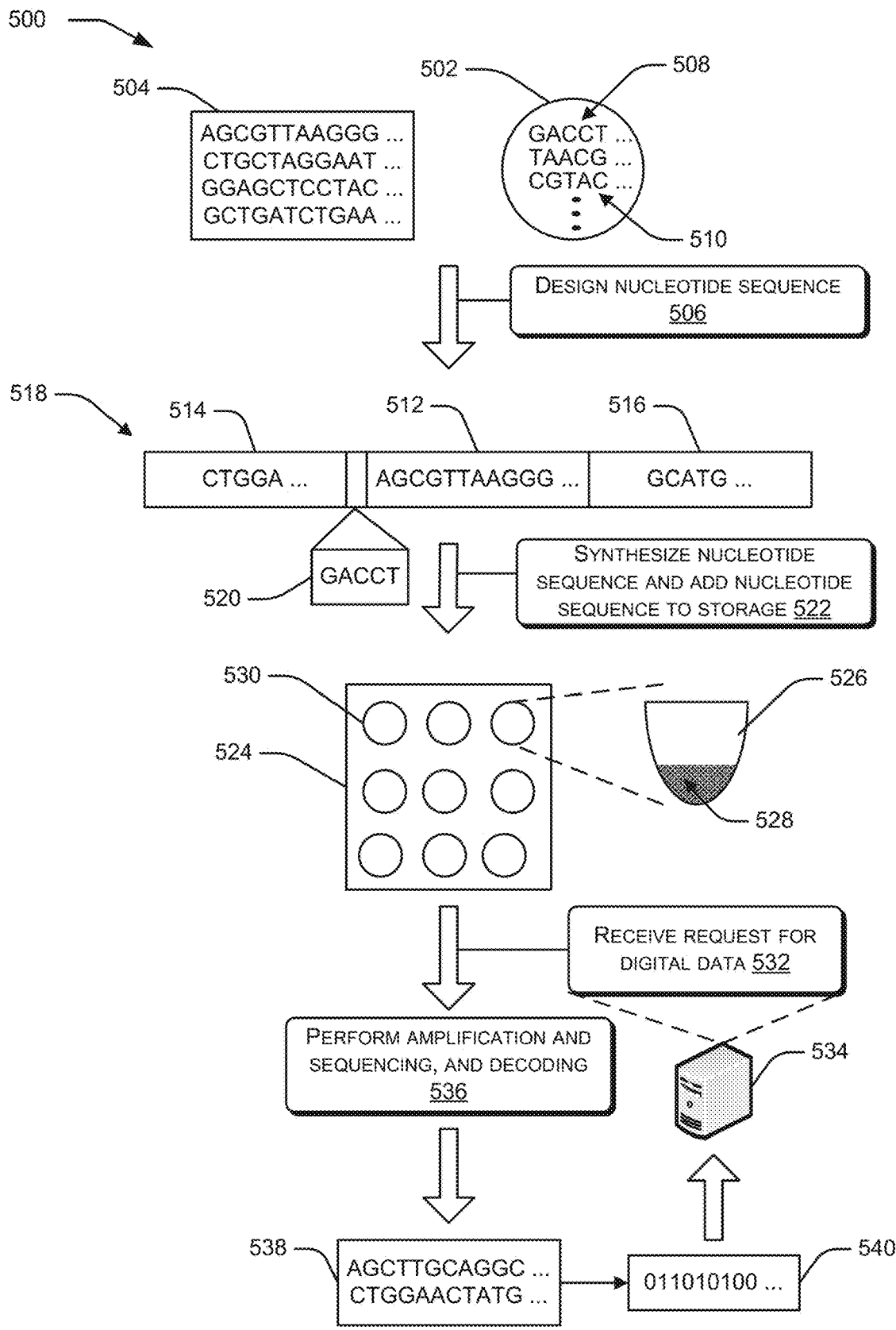
FIG. 5 shows a schematic representation of an example process to assemble polynucleotide sequences using a group of primers and a number of information payloads. (SEQ ID NOs: 1-6)

FIG. 5 shows a schematic representation of an example process 500 to design polynucleotide sequences using a group of primers 502 and a number of payloads 504 that encode digital data. At 506, a first primer 508 and a second primer 510 can be associated with a payload 512. A first primer target 514 that is complementary to the first primer 508 and a second primer target 516 that is complementary to the second primer 510 can be generated to produce a polynucleotide sequence 518. The first primer target 514 can be placed at a 5' end of the polynucleotide sequence 518 and the second primer target 516 can be placed at a 3' end of the polynucleotide sequence 518. In some implementations, additional nucleotides 520 can be included in the polynucleotide sequence 518, where the additional nucleotides 520 encode additional information. For example, at least a portion of the additional nucleotides 520 can encode addressing information. In another example, at least a portion of the additional nucleotides 520 can encode error correction information. Although the position of the additional nucleotides 520 is shown between the first primer target 514 and the payload 512, the additional nucleotides 520 can be positioned at one or more different positions of the polynucleotide sequence 518.

At 522, the process 500 includes synthesizing the polynucleotide sequence 518 and adding the polynucleotide sequence 518 to a polynucleotide storage system 524. Synthesizing the polynucleotide sequence 518 can include chemically bonding the nucleotides of the polynucleotide sequence 518 together in a linear chain. The polynucleotide storage system 524 can include a number of containers, such as container 526. Container 526 can include a medium 528 that stores a number of different polynucleotide sequences. The medium 528 can include any medium that can maintain the chemical bonding and structure of polynucleotide sequences over an extended period of time, such as several years, several decades, or longer. In some implementations, the medium 528 can include water. In some implementations, the polynucleotide storage system 524 can store polynucleotide sequences using a media free arrangement, such as storing dried polynucleotide pellets.

In some implementations, the container 524 can store a number of polynucleotide sequences. Also, the container 524 can store multiple copies of a polynucleotide sequence, such as the polynucleotide sequence 518. Additionally, in various implementations, more than one of the containers of the polynucleotide storage system 524 can store a polynucleotide sequence. To illustrate, the container 526 and an additional container 530 of the polynucleotide storage system 524 can each store separate copies of the polynucleotide sequence 518. In some implementations, polynucleotides stored in the container 524 can have melting points within a first range, while polynucleotides stored in the additional container 530 can have melting points within a second range. Thus, the polynucleotides of the container 524 and polynucleotides of the additional container 530 can be stored and retrieved based on their different melting points.

At 532, the process 500 includes receiving a request for digital data. The request for digital data can be received from a computing device, such as computing device 534. After receiving the request for the digital data, the one or more polynucleotide sequences that correspond to the digital data can be determined using a lookup table or other data structure that indicates the polynucleotide sequences that encode the requested digital data. For example, a data structure can indicate that a data file is encoded by a group of polynucleotides and that the group of polynucleotides are associated with respective primer targets and/or respective keys that, at least partially, correspond to the primer targets. A data structure can also indicate the locations of polynucleotides stored within the container 524.

At 536, the process 500 can include amplification of target polynucleotide sequences corresponding to the requested digital data using primers associated with the target polynucleotide sequences, sequencing of the polynucleotide sequences produced in the amplification operation, and decoding the polynucleotide sequences to produce the requested digital data. The amplification of the target polynucleotide sequences can take place using primers that include nucleotides that are complementary to the primer targets associated with the target polynucleotide sequences. In some implementations, the primers and enzymes used to replicate sequences can be added to one or more containers of the data storage system 624 or to one or more other containers that include the polynucleotide sequences that correspond to the requested digital data. In other implementations, the polynucleotide sequences to be replicated and amplified can be moved to another container and/or medium in order to perform the replication and amplification processes. In an illustrative example, PCR can be used to amplify the polynucleotide sequences that correspond to the requested digital data.

A PCR reaction has three main components: the template, the primers, and enzymes. The template is a single- or double-stranded molecule containing the (sub)sequence of nucleotides to be amplified. The primers are short synthetic strands that define the beginning and end of the region to be amplified. The enzymes include polymerases and thermostable polymerases such as DNA polymerase, RNA polymerase and reverse transcriptase. The enzymes create double-stranded polynucleotides from a single-stranded template by "filling in" complementary nucleotides one by one through addition of nucleoside triphosphates, starting from a primer bound to that template. PCR happens in "cycles," each of which doubles the number of templates in a solution. The process can be repeated until the desired number of copies is created.

A variety of PCR techniques are known and can be used in the implementations described herein. PCR techniques are typically used for the amplification of at least a portion of a polynucleotide. The sample to be amplified is contacted with the first and second primers; a nucleic acid polymerase; and nucleotide triphosphates corresponding to the nucleotides to be added during PCR. Natural nucleotide triphosphates can include dATP, dCTP, dGTP, dTTP, and dUTP. Nucleoside triphosphates of non-standard nucleotides can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

An additional type of PCR is Droplet Digital™ PCR (ddPCR™) (Bio-Rad Laboratories, Hercules, Calif.). ddPCR technology uses a combination of microfluidics and surfactant chemistry to divide PCR samples into water-in-oil droplets. The droplets support PCR amplification of the target template nucleotides they contain and use reagents and workflows similar to those used for most standard Taqman probe-based assays. Following PCR, each droplet is analyzed or read in a flow cytometer to determine the fraction of PCR-positive droplets in the original sample. These data are then analyzed using Poisson statistics to determine the target concentration in the original sample. See Bio-Rad Droplet Digital™ (ddPCR™) PCR Technology.

While ddPCR™ is one PCR approach, other sample partition PCR methods based on the same underlying principles may also be used. The partitioned nucleotides of a sample can be amplified by any suitable PCR methodology that can be practiced within spdPCR. Illustrative PCR types include allele-specific PCR, assembly PCR, asymmetric PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, single-cell PCR, solid-phase PCR, thermal asymmetric interlaced PCR, touchdown PCR, universal fast walking PCR, etc. Ligase chain reaction (LCR) can also be used.

The amplification of polynucleotide sequences can be performed using a thermocycler. A thermocycler (also known as a thermal cycler, PCR machine, or DNA amplifier) can be implemented with a thermal block that has holes where tubes holding an amplification reaction mixture can be inserted. The term "amplification reaction mixture" can refer to an aqueous solution comprising the various reagents used to amplify a target nucleic acid. The thermocycler 104 can then raise and lower the temperature of the block in discrete, pre-programmed steps. Other implementations can utilize a miniaturized thermocycler in which the amplification reaction mixture moves via a channel through hot and cold zones on a microfluidic chip.

After the amplification process, one or more samples of the amplification product can be extracted and sequenced by a sequencer using any of the techniques described below. The sequencer can provide raw sequence data output referred to herein as reads. Each position in a read is an individual nucleotide determined by the sequencer based on properties of the nucleotides sensed by components of the sequencer. The properties sensed by the sequencer can vary depending on the specific sequencing technology used. A read can represent a determination of which of the four nucleotides—A, G, C, and T (or U)—in a strand of DNA (or RNA) is present at a given position in the sequence. The sequencer can produce polynucleotide sequences 538 that correspond to the requested data. The polynucleotide sequences 538 can be decoded using a reverse process that was used to encode the original digital data to produce a bit string 540 that corresponds to the original digital data. The bit string 540 can be provided to the computing device 534 in response to the request for the digital data. The sequencing of polynucleotides can be implemented using any of the following sequencing technologies or another technology besides those specifically mentioned here.

In some implementations, a sequencing technology utilized in sequencing operations described herein can include sequencing-by-synthesis (Illumina® sequencing). Sequencing by synthesis is based on amplification of DNA on a solid surface using fold-back PCR and anchored primers. The DNA is fragmented, and adapters are added to the 5'- and 3'-ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technique that can be used in implementations described herein is nanopore sequencing. A nanopore is a small hole of the order of 1 nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technology that can be used in implementations described herein includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure that enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another sequencing technique that can be used in implementations described herein is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into an instrument, e.g., a HeliScope™ sequencer, and a laser illuminates the surface of the flow cell, revealing the position of each template. A CCD camera can map the position of the templates on the flow cell surface. The template fluorescent-label is then cleaved and washed away. The sequencing reaction begins by introducing a DNA polymerase and a fluorescently-labeled nucleotide. The oligo-T nucleic acid serves as a primer. The polymerase incorporates the labeled nucleotides to the primer in a template-directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently-labeled nucleotides until the desired read length is achieved. Sequence information is collected with each nucleotide addition step.

Another example of a DNA sequencing technique that can be used is SOLiD™ technology (Applied Biosystems). In SOLiD™ sequencing, DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, templates, and PCR components. Following PCR, the templates are denatured and beads are enriched to separate the beads with extended templates. Templates on the selected beads are subjected to a 3' modification that permits bonding to a glass slide.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an ion-sensitive field effect transistor (ISFET) to sequence DNA. Ion Torrent™ sequencing is an example of this technique. In this technique, no labelling molecules are necessary and during DNA synthesis incorporation of each nucleotide is detected. In succession, either adenine, cytosine, guanine, or thymine is flowed through the DNA chamber, and if a nucleotide becomes incorporates into the nascent strand, the reaction emits a hydrogen ion. The hydrogen ion emission is detected, and this indicates which based became incorporated at a given position.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

Figure 6:
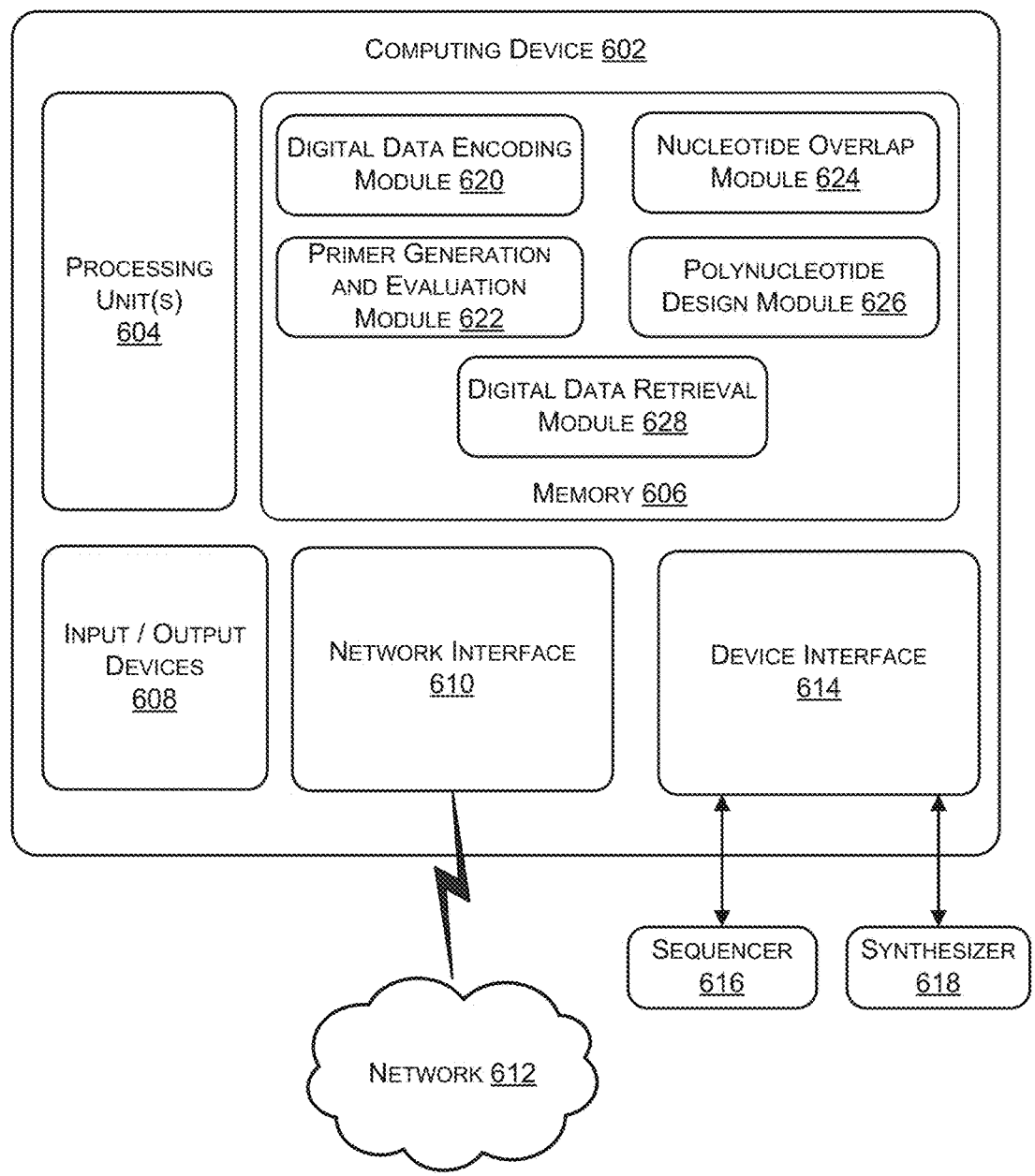
FIG. 6 shows a block diagram of an example computing device to produce polynucleotide sequences used to store data.

FIG. 6 shows a block diagram of an example system 600 including a computing device 602 to produce polynucleotide sequences used to store data. The computing device 602 can be implemented with one or more processing unit(s) 604 and memory 606, both of which can be distributed across one or more physical or logical locations. For example, in some implementations, the operations described as being performed by the computing device 602 can be performed by multiple computing devices. In some cases, the operations described as being performed by the computing device 602 can be performed in a cloud computing architecture.

The processing unit(s) 604 can include any combination of central processing units (CPUs), graphical processing units (GPUs), single core processors, multi-core processors, application-specific integrated circuits (ASICs), programmable circuits such as Field Programmable Gate Arrays (FPGA), and the like. In one implementation, one or more of the processing units(s) 604 can use Single Instruction Multiple Data (SIMD) parallel architecture. For example, the processing unit(s) 604 can include one or more GPUs that implement SIMD. One or more of the processing unit(s) 604 can be implemented as hardware devices. In some implementations, one or more of the processing unit(s) 604 can be implemented in software and/or firmware in addition to hardware implementations. Software or firmware implementations of the processing unit(s) 604 can include computer- or machine-executable instructions written in any suitable programming language to perform the various functions described. Software implementations of the processing unit(s) 604 may be stored in whole or part in the memory 606.

Alternatively, or additionally, the functionality of computing device 602 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 606 of the computing device 602 can include removable storage, non-removable storage, local storage, and/or remote storage to provide storage of computer-readable instructions, data structures, program modules, and other data. The memory 606 can be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media can embody computer-readable instructions, data structures, program modules, or other data in a modulated data signal, such as a carrier wave, or other transmission mechanism. As defined herein, computer-readable storage media and communications media are mutually exclusive.

The computing device 602 can include and/or be coupled with one or more input/output devices 608 such as a keyboard, a pointing device, a touchscreen, a microphone, a camera, a display, a speaker, a printer, and the like. Input/output devices 608 that are physically remote from the processing unit(s) 604 and the memory 606 can also be included within the scope of the input/output devices 608.

Also, the computing device 602 can include a network interface 610. The network interface 610 can be a point of interconnection between the computing device 602 and one or more networks 612. The network interface 610 can be implemented in hardware, for example, as a network interface card (NIC), a network adapter, a LAN adapter or physical network interface. The network interface 610 can be implemented in software. The network interface 610 can be implemented as an expansion card or as part of a motherboard. The network interface 610 can implement electronic circuitry to communicate using a specific physical layer and data link layer standard, such as Ethernet or Wi-Fi. The network interface 610 can support wired and/or wireless communication. The network interface 610 can provide a base for a full network protocol stack, allowing communication among groups of computers on the same local area network (LAN) and large-scale network communications through routable protocols, such as Internet Protocol (IP).

The one or more networks 612 can include any type of communications network, such as a local area network, a wide area network, a mesh network, an ad hoc network, a peer-to-peer network, the Internet, a cable network, a telephone network, a wired network, a wireless network, combinations thereof, and the like.

A device interface 614 can be part of the computing device 602 that provides hardware to establish communicative connections to other devices, such as a sequencer 616, a polynucleotide synthesizer 618, etc. The device interface 614 can also include software that supports the hardware. The device interface 614 can be implemented as a wired or wireless connection that does not cross a network. A wired connection may include one or more wires or cables physically connecting the computing device 602 to another device. The wired connection can be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like.

The computing device 602 can include multiple modules that may be implemented as instructions stored in the memory 606 for execution by processing unit(s) 604 and/or implemented, in whole or in part, by one or more hardware logic components or firmware. The memory 606 can be used to store any number of functional components that are executable by the one or more processors processing units 604. In many implementations, these functional components comprise instructions or programs that are executable by the one or more processing units 604 and that, when executed, implement operational logic for performing the operations attributed to the computing device 602. Functional components of the computing device 602 that can be executed on the one or more processing units 604 for implementing the various functions and features related to generating polynucleotide sequences for the storage and retrieval of digital data, as described herein, include a digital data encoding module 620, a primer generation and evaluation module 622, a nucleotide overlap module 624, a polynucleotide design module 626, and a digital data retrieval module 628. One or more of the modules, 620, 622, 624, 626, 628 can be used to implement processes 100, 200, 400, and at least a portion of the process 500 of FIG. 1, FIG. 2, FIG. 4, and FIG. 5.

The digital data encoding module 620 can include computer-readable instructions that are executable by the processing unit(s) 604 to encode digital data as a sequence of nucleotides. The digital data encoding module 620 can obtain digital data from one or more sources. In some cases, the digital data can also be stored by the memory 606. Also, the digital data can be stored by a data storage device coupled to, or otherwise accessible to, the computing device 602. The digital data can be related to image content, video content, text content, audio content, combinations thereof, and so forth. The digital data can include a bit string comprised of 1s and 0s.

The digital data encoding module 620 can encode the 1s and 0s of the digital data to a sequence of nucleotides, such as A, T, G, C, or U. In particular implementations, each 1 or 0 of the digital data can be encoded as a particular nucleotide. In some cases, groups of 1s and groups of 0s of the digital data can be encoded as a particular nucleotide. In various implementations, the 1s and 0s of the digital data can be converted to a number in a number system other than base 2 before encoding. For example, the 1s and 0s of the digital data can be converted to a base-3 format or a base-4 format before encoding.

In illustrative implementations, the digital data encoding module 620 can encode the 1s and 0s of the digital data according to a binary encoding scheme. For example, the digital data encoding module 620 can encode the series of bits 00 as a first nucleotide (e.g., A), the series of bits 01 as a second nucleotide (e.g., T), the series of bits 10 as a third nucleotide (e.g., G), and the series of bits 11 as a fourth nucleotide (e.g., C).

In other illustrative implementations, the digital data encoding module 620 can encode the 1s and 0s of the digital data according to a ternary encoding scheme. For example, the digital data encoding module 620 can convert the 1s and 0s of the digital data to modified digital data comprising 0s, 1s, and 2s. Subsequently, the digital data encoding module 620 can encode the 0s, 1s, and 2s of the modified digital data as nucleotides. In some implementations, the data encoding module 620 can encode the 0s, 1s, and 2s of the modified digital data as nucleotides according to a preceding nucleotide in the sequence of nucleotides. To illustrate, a 0 preceded by G could be encoded as T, while a 0 preceded by A could be encoded as C.

In additional illustrative implementations, the digital data encoding module 620 can encode the 1s and 0s of the digital data according to a base-4 encoding scheme. In an example, the digital data encoding module 620 can convert the 1s and 0s of the digital data to modified digital data comprising 0s, 1s, 2s, and 3s. In these situations, when 4 nucleotides are used to encoded the digital data, each type of nucleotide being used to do the encoding can correspond with a respective base-4 number. Thus, in a particular illustrative example, 0 can correspond with A, 1 can correspond with T, 2 can correspond with G, and 3 can correspond with C.

In some cases, the length of the sequences of nucleotides encoding the digital data can be limited. For example, if the length of the sequence of nucleotides encoding the digital data is greater than a particular number of nucleotides, the sequence can become unstable and/or otherwise lose its linear arrangement, such as by forming secondary structures. In illustrative implementations, the sequences of nucleotides used to encode digital data can have from 60 to 150 nucleotides, from 80 to 130 nucleotides, from 90 to 120 nucleotides, or from 100 to 140 nucleotides. In situations where multiple sequences are used to encode the digital data, the digital data encoding module 620 can divide the bits of the digital data into segments. The digital data encoding module 620 can encode each of the segments of the digital data as a separate sequence of nucleotides. In some cases, the segments can be the same length, while in other situations, the segments can have varying lengths.

The primer generation and evaluation module 622 can include computer-readable instructions that, when executed by the processing unit(s) 604, can generate nucleotide sequences for primers and evaluate the primers according to one or more primer evaluation criteria. The primer generation module 622 can generate nucleotides sequences of a particular length that can be utilized as primers for polynucleotides used in the storage and retrieval of digital data by polynucleotide sequences. For example, the primer generation and evaluation module 622 can generate sequences of nucleotides having a length from 18 to 30 nucleotides. In another example, the primer generation module 622 can generate sequences of nucleotides having a length from 20 to 25 nucleotides. The primer generation and evaluation module 622 can generate sequences of nucleotides using one or more pseudo-random number algorithms. In some cases, the primer generation and evaluation module 622 can generate hundreds up to thousands of sequences of nucleotides. In various implementations, the sequences of nucleotides generated by the primer generation and evaluation module 622 can include nucleotide sequences having repeated nucleotides. To illustrate, the primer generation and evaluation module 622 can generate sequences of nucleotides including two or more A's, two or more G's, two or more C's, two or more T's, or combinations thereof.

The primer generation and evaluation module 622 can evaluate primers according to a number of primer evaluation criteria. In some cases, at least a portion of the primers evaluated by the primer generation and evaluation module 622 can be generated by sources other than the primer generation and evaluation module 622. For example, a third-party service provider can provide the primers to be evaluated by the primer generation and evaluation module 622. Additionally, at least a portion of the primers evaluated by the primer generation and evaluation module 622 according to the primer evaluation criteria can be generated by the primer generation and evaluation module 622. The primer evaluation criteria can include G/C content of the primers, melting temperature of the primers, secondary structure formation by the primers, primer-dimer formation by the primers, length of A/T regions of the primers, length of G/C regions of the primers, differentiation between nucleotides of the respective primers, similarity between sequences of nucleotides of the primers, or combinations thereof.

In implementations, the primer generation and evaluation module 622 can evaluate primers by comparing values of criteria for the primers with specified values for one or more of the primer evaluation criteria. The specified values of the primer evaluation criteria that are used by the primer generation and evaluation module 622 to evaluate the primers can be based at least partly on the effect that values of the various criteria can have on the accuracy and/or efficiency of a polynucleotide replication and amplification process, such as PCR. For example, a melting temperature of primers within a particular range can increase the accuracy and/or efficiency of a polynucleotide replication process. In these situations, the primer generation and evaluation module 622 can evaluate the primers by comparing the melting temperatures of the primers to the particular range of melting temperatures to determine whether or not the melting temperatures of the primers are within the particular range. In another example, G/C content of primers within a particular range can increase the accuracy and/or efficiency of a polynucleotide replication process. In these scenarios, the primer generation and evaluation module 622 can evaluate the primers by comparing the G/C content of the primers to the particular range of G/C content to determine whether or not the G/C content of the primers are within the particular range.

The evaluation of primers by the primer generation and evaluation module 622 can generate scoring for the primers being evaluated. In some implementations, the primer generation and evaluation module 622 can generate a score for each of the primers being evaluated. In particular implementations, the primer generation and evaluation module 622 can generate scores for primers based on each of the primer evaluation criteria. For example, the primer generation and evaluation module 622 can determine a first score for a primer with respect to a melting temperature criteria, a second score for the primer with respect to a G/C content criteria, a third score for the primer with respect to a secondary structure criteria, and so forth. In various implementations, the primer generation and evaluation module 622 can generate a score for the individual nucleotides included in the primers with respect to the primer evaluation criteria. To illustrate, the primer generation and evaluation module 622 can generate scores for individual nucleotides of a primer with respect to a melting temperature criteria. In another illustration, the primer generation and evaluation module 622 can generate scores for individual nucleotides of a primer with respect to a primer-dimer formation criteria.

The primer generation and evaluation module 622 can identify primers to be used in replicating and amplifying polynucleotide sequences that encode digital data based at least partly on the evaluations of the primers. In some implementations, the primer generation and evaluation module 622 can identify primers to be used in the replication and amplification of polynucleotide sequences that can encode digital data based at least partly on scores associated with the primers, where the scores have been determined by the primer generation and evaluation module 622. In various implementations, the primer generation and evaluation module 622 can compare a score for an individual primer with a threshold score to determine whether or not the primer is to be used in the replication and amplification of a polynucleotide sequence that encodes digital data. In particular implementations, the threshold score can be based at least partly on a probability that a primer can adversely affect polynucleotide replication and amplification operations. The primer generation and evaluation module 622 can determine that a score for a primer is less than a threshold score and add the primer to a group of primers that is used in replicating and amplifying polynucleotide sequences that encode digital data. The primer generation and evaluation module 622 can also determine a score for a primer that meets or exceeds the threshold score and remove the primer from consideration to be used in the replication and amplification of a polynucleotide sequence used to encode digital data.

The primer generation and evaluation module 622 can modify primers that have scores less than the threshold score to generate additional primers having scores less than the threshold score. In some implementations, the primer generation and evaluation module 622 can modify one or more nucleotides of a primer having a score less than the threshold score to produce a new primer and then evaluate the new primer based on the primer evaluation criteria. The primer generation and evaluation module 622 can continue to modify nucleotides of primers having scores less than the threshold score until the scores of the primers increase and/or until scores of the primers meet or exceed the threshold score. Additionally, the primer generation and evaluation module 622 can modify one or more nucleotides of a primer to decrease the score for the primer until the score for the primer is less than the threshold score. For example, the primer generation and evaluation module 622 can identify nucleotides that cause the score for the primer to be above the threshold score and modify the nucleotides such that the score for the primer moves below the threshold score.

The primer generation and evaluation module 622 can also generate primer targets based on the primers having scores that are below the threshold score. That is, for each primer to be used in polynucleotide replication and amplifications, a corresponding primer target can be generated. The primer targets can include sequences of polynucleotides that are complementary to the sequences of the primers. In some cases, some, but not all of the nucleotides of the primer targets are complementary to the nucleotides of the primers. To illustrate, a threshold amount of the nucleotides of the primer targets are complementary to the nucleotides of the primers.

The nucleotide overlap module 624 can include computer-readable instructions that when executed by the processing unit(s) 604 can determine an amount of overlap between primer targets and payloads. The amount of overlap can indicate a number of nucleotides of a primer target and a number of nucleotides of a payload that are the same in corresponding positions. The nucleotide overlap module 624 can compare individual nucleotides of the primer target with individual nucleotides of a payload. In particular implementations, the nucleotide overlap module 624 can compare a nucleotide of a primer target at a particular position with a nucleotide of the payload at the same position. The nucleotide overlap module 624 can determine that there is overlap between the primer target and the payload when the nucleotide at the position is the same.

In an illustrative implementation, an amount of sequence identity between a primer target and a payload can be determined by performing a number of iterations of comparisons between nucleotides at various positions of the primer target and corresponding positions of the payload. In a first iteration, nucleotides of the primer target can be compared with a first region of nucleotides of a payload to determine any matches between the nucleotides being compared. In a second iteration, the nucleotides of the primer target can be compared with a second region of nucleotides of the payload to determine any matches between the nucleotides being compared. In some situations, the first region of nucleotides of the payload and the second region of nucleotides of the payload can include one or more different nucleotides. The comparisons between the nucleotides of the primer target and the payload can continue until each of the nucleotides of the payload have been compared with at least one of the nucleotides of the primer target. In some illustrative implementations, a BLAST tool can be utilized to determine an amount of sequence identity between a primer target and a payload. In particular implementations, the amount of sequence identity between the different regions of the payload can be compared with one another. To illustrate, the amount of sequence identity between the first region of the payload and the primer target can be compared with the amount of sequence identity between the second region of the payload and the primer target. In some situations, the region of the payload having the highest amount of sequence identity with the primer target can be modified to decrease the amount of sequence identity between that region of the payload and the primer target.

The nucleotide overlap module 624 can also determine that a primer corresponding to a primer target can be included in a group of primers to be used in polynucleotide sequences encoding digital data based on the amount of overlap between the primer target and one or more payloads being less than a threshold amount of overlap. In some cases, the threshold amount of overlap can correspond to a probability that a primer target having a particular amount of overlap with a payload can adversely affect polynucleotide sequence replication and amplification operations. The nucleotide overlap module 624 can determine that an amount of overlap between nucleotides of a primer target and nucleotides of one or more payloads are less than the threshold amount of overlap and add a primer corresponding to the primer target to a group or primers to be used in generating polynucleotides sequences using the one or more payloads to encode digital data. Additionally, the nucleotide overlap module 624 can determine that an amount of overlap between nucleotides of a primer target and nucleotides of one or more payloads meet or exceed a threshold amount of overlap and indicate that a primer corresponding to the primer target is not to be added to a group of primers to generate polynucleotide sequences using the one or more payloads to encode digital data. In various implementations, the threshold amount of overlap can correspond to a number of consecutive positions of primer targets and payloads that have the same nucleotide. For example, a threshold amount of overlap can correspond to 10 positions of a primer target having a nucleotide that matches a 10-nucleotide region of a payload. In other implementations, the threshold amount of overlap can account for mismatches and gaps within the sequences of the primer targets and the payloads can correspond to an overall number of positions where the nucleotides of the primer targets match one or more regions of the payloads. To illustrate, a threshold amount of overlap can correspond to 15 positions of a 40-nucleotide primer target having the same nucleotide at least one 40-nucleotide region of a payload.

The nucleotide overlap module 624 can also determine an amount of overlap between primers themselves and payloads by analyzing thermodynamic characteristics of the primers and the payloads. The thermodynamic characteristics can indicate a probability that a primer may bind to a payload instead of binding to a primer target. The thermodynamic characteristics analyzed by the nucleotide overlap module 624 can include entropy, enthalpy, Gibbs free energy, or combinations thereof.

The polynucleotide design module 626 can include computer-readable instructions that, when executed by the processing unit(s) 604, design polynucleotide sequences that encode digital data. The polynucleotide design module 626 can utilize payloads produced by the digital data encoding module 620 to design the polynucleotide sequences. The polynucleotide design module 626 can also utilize primers from a group of primers that is produced based on the evaluations of primers performed by the primer generation and evaluation module 622 and based on amounts of overlap determined by the nucleotide overlap module 624. The primers can be used to generate primer targets that can be included in the polynucleotide sequences. In some implementations, the polynucleotide design module 626 can produce a polynucleotide sequence used to encode digital data by identifying two primers and a payload. A first primer can correspond to a first primer target that is to be located on a 3' end of a polynucleotide sequence and a second primer can correspond to a second primer target that is to be located on a 5' end of a polynucleotide sequence with the payload being located between the two primer targets.

The polynucleotide design module 626 can also produce polynucleotide sequences that include nucleotides in addition to the nucleotides of the primer targets and the payloads. For example, the polynucleotide design module 626 can include nucleotides in a polynucleotide sequence that correspond with addressing information for the payload. In situations where a string of bits is divided into a number of segments before being encoded as a sequence of nucleotides, addressing information can indicate the segment of the bit string that is being encoded by a particular payload and the location of the segment within the bit string. The polynucleotide design module 626 can generate one or more nucleotides that encode the addressing information and add the nucleotides encoding the addressing information into a polynucleotide sequence. In particular implementations, addressing information can be included, at least partially, in primer targets. The primer targets can also include nucleotides that correspond to a key that can be used to retrieve the digital data encoded by a payload of a polynucleotide sequence. The polynucleotides design module 626 can also add nucleotides to a polynucleotide sequence that corresponds to error correction information.

The polynucleotide sequences generated by the polynucleotide design module 626 can be used to synthesize molecules that include polynucleotides sequences. In some implementations, the polynucleotide design module 626 can communicate polynucleotide sequences to one or more devices, such as device 618, used to synthesize the polynucleotide sequences. For example, the polynucleotide design module 626 can communicate polynucleotide sequences to a service provider that synthesizes polynucleotide sequences via the one or more networks 612. In another example, the polynucleotide design module 626 can communicate polynucleotides sequences to a device that synthesizes polynucleotide sequences via the one or more networks 612 and/or to one or more devices (e.g., synthesizer 618) via the device interface 614.

The digital data retrieval module 628 can include computer-readable instructions that when executed by the processing unit(s) 604 can provide digital data in response to a request for the digital data. In some implementations, the digital data retrieval module 628 can receive a request to obtain digital data. For example, the digital data retrieval module 628 can receive a request for a data file including a digital image. The digital data retrieval module 628 can identify one or more polynucleotide sequences that correspond to the requested data. To illustrate, the digital data retrieval module 628 can parse a data structure, such as a lookup table, to identify the primers, addressing information, and/or keys that correspond to the requested digital data. The digital data retrieval module 628 can communicate with one or more devices, such as via the device interface 614, to request the polynucleotide sequences that correspond to the primers, addressing information, and/or keys. The digital data retrieval module 628 can receive the polynucleotide sequences from one or more devices, such as device 618, and decode the polynucleotide sequences using a reverse process from the encoding performed by the digital data encoding module 620. For example, in implementations where 00 in a string of bits is encoded as A, the digital data retrieval module 628 can decode each A in the polynucleotide sequences as 00. The digital data retrieval module 628 can reproduce the bit string of the digital data being requested and provide the bit string to one or more devices that requested the digital data.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause A. A method comprising: generating data indicating a primer sequence; determining a score for the primer sequence based at least partly on an estimated melting temperature of the potential primer sequence and one or more additional criteria; and adding the primer sequence to a group of primers based at least partly on the score being less than a threshold score.

Clause B. The method of clause A, wherein determining the score for the primer sequence includes: determining a respective score for individual nucleotides of the primer sequence; combining the respective scores for the individual nucleotides to determine an aggregate score; and determining that the aggregate score is at least the threshold score based at least partly on a comparison between the aggregate score and the threshold score.

Clause C. The method of clause B, wherein the threshold score indicates a probability that the primer sequence affects the specificity of a polynucleotide sequence amplification operation.

Clause D. The method of clause A, wherein determining the score for the primer sequence includes: determining a first score for a nucleotide of the primer sequence based at least partly on the estimated melting temperature of the primer sequence; and determining a second score for the nucleotide based at least partly on one of the one or more additional criteria.

Clause E. The method of clause A, wherein determining the score for the primer sequence based at least partly on the estimated melting temperature of the primer sequence includes determining that the melting temperature is included in a range of melting temperatures.

Clause F. The method of clause D, wherein the range of the melting temperatures is from 50° C. to 65° C.

Clause G. The method of clause A, further comprising: modifying, based at least partly on the score being less than the threshold score, at least one nucleotide of the primer sequence to produce a modified primer sequence; and determining an additional score for the modified primer sequence based at least partly on an additional estimated melting temperature of the modified primer sequence and the one or more additional criteria.

Clause H. The method of clause G, further comprising: adding the modified primer sequence to the group of primers at least partly based on the additional score being below the threshold score; and generating a polynucleotide sequence including at least one primer target complementary to at least one of the primer sequence or the modified primer sequence, the polynucleotide sequence also including a payload having another sequence of nucleotides that encodes digital data.

Clause I. A system comprising: a processing unit; a memory in communication with the processing unit, the memory storing computer-readable instructions that when executed by the processing unit perform operations comprising: generating data including a sequence of nucleotides for a primer; determining a respective score for individual nucleotides of the primer for individual criteria of a plurality of criteria, the plurality of criteria being related to a fitness of sequences of nucleotides to be used in polynucleotide sequence amplification and replication; aggregating the respective scores for the individual nucleotides of the primer with respect to the individual criteria of the plurality of criteria to produce an aggregated score; determining that the aggregated score is less than a threshold score; and generating a polynucleotide sequence that includes a primer target at least partially complementary to the primer, an additional primer target at least partially complementary to an additional primer having an additional aggregated score less than the threshold score, and a payload including a nucleotide sequence that encodes digital data.

Clause J. The system of clause I, wherein the plurality of criteria includes secondary structure formation; and operations further comprise: determining a score for a nucleotide of the primer based at least partly on a probability of the nucleotide participating in the formation of a secondary structure.

Clause K. The system of clause I, wherein the plurality of criteria includes primer-dimer formation, and the operations further comprise: determining a score for a nucleotide of the primer based at least partly on a probability of the primer forming a dimer with another primer.

Clause L. The system of clause I, wherein the plurality of criteria includes length of A/T regions of the sequence of nucleotides, and the operations further comprise: determining that a nucleotide included in the primer is an A or a T; determining that the nucleotide is included in a region of the primer that consists of one or more A's and one or more T's; determining a length of the region; and determining a score for a nucleotide based at least partly on the length of the region.

Clause M. The system of clause I, wherein the plurality of criteria includes length of G/C regions of the sequence of nucleotides, and the operations further comprise: determining that a nucleotide included in the primer is a G or a C; determining that the nucleotide is included in a region of the primer that consists of one or more G's and one or more C's; determining a length of the region; and determining a score for a nucleotide based at least partly on the length of the region.

Clause N. The system of clause I, wherein the plurality of criteria includes G/C content, and the operations further comprise: determining a number nucleotides included in the primer that are G and C in relation to the total number of nucleotides included in the primer; and determining a score for the nucleotide based at least partly on the nucleotide being a G or a C and the number of nucleotides in the primer that are G or C in relation to the total number of nucleotides of the primer.

Clause O. The system of clause I, wherein the plurality of criteria includes nucleotide differentiation, and the operations further comprise: comparing a nucleotide of the primer with one or more additional nucleotides included in the primer; and determining a score for the nucleotide based at least partly on differences between the nucleotide and the one or more additional nucleotides.

Clause P. The system of clause I, wherein the plurality of criteria includes primer similarity, and the operations further comprise: comparing nucleotides of the primer with nucleotides of an additional primer; determining a number of nucleotides of the primer that are the same as the nucleotides of the additional primer and that are located in the same positions; and determining a score for the nucleotide based at least partly on the number of nucleotides of the primer that are the same as the nucleotides of the additional primer and that are located in the same positions.

Clause Q. A method comprising: determining one or more characteristics of a first primer sequence; determining a score for the first primer sequence based at least partly on the one or more characteristics in relation to one or more criteria, wherein the one or more criteria indicate a fitness of the first primer sequence to be utilized in polynucleotide sequence amplification; determining that the score is less than a threshold score; adding the first primer sequence to a group of primers; and generating a polynucleotide sequence including a first primer target corresponding to the first primer sequence, a second primer target corresponding to a second primer sequence from the group of primers, and a payload including an additional sequence of nucleotides that encodes digital data.

Clause R. The method of clause Q, wherein individual primers included in the group of primers are associated with a respective score that is less than the threshold score.

Clause S. The method of clause Q, further comprising: receiving, from a computing device, a request for the digital data; parsing a data structure to determine that the first primer sequence and the second primer sequence are associated with the digital data; amplifying one or more polynucleotides included in a container of a polynucleotide storage system using the one or more enzymes, the first primer sequence, and the second primer sequence; sequencing the one or more polynucleotide sequences; decoding the one or more polynucleotide sequences to identify a series of bits corresponding to the digital data; and providing the series of bits to the computing device.

Clause T. The method of clause Q, wherein a first group of polynucleotides stored in a first container of the polynucleotide storage system have a first range of melting temperatures and a second group of polynucleotides stored in a second container of the polynucleotide storage system have a second range of melting temperatures.

Clause U. A system comprising: means for generating data including a sequence of nucleotides for a primer; means for determining a respective score for individual nucleotides of the primer for individual criteria of a plurality of criteria, the plurality of criteria being related to a fitness of sequences of nucleotides to be used in polynucleotide sequence amplification and replication; means for aggregating the respective scores for the individual nucleotides of the primer with respect to the individual criteria of the plurality of criteria to produce an aggregated score; means for determining that the aggregated score is less than a threshold score; and means for generating a polynucleotide sequence that includes a primer target at least partially complementary to the primer, an additional primer target at least partially complementary to an additional primer having an additional aggregated score less than the threshold score, and a payload including a nucleotide sequence that encodes digital data.

Clause V. The system of clause U, further comprising: means for determining a score for a nucleotide of the primer based at least partly on a probability of the nucleotide participating in the formation of a secondary structure.

Clause W. The system of clause U, wherein the plurality of criteria includes primer-dimer formation, and the system further comprises: means for determining a score for a nucleotide of the primer based at least partly on a probability of the primer forming a dimer with another primer.

Clause X. The system of clause U, wherein the plurality of criteria includes length of A/T regions of the sequence of nucleotides, and the system further comprises: means for determining that a nucleotide included in the primer is an A or a T; means for determining that the nucleotide is included in a region of the primer that consists of one or more A's and one or more T's; means for determining a length of the region; and means for determining a score for a nucleotide based at least partly on the length of the region.

Clause Y. The system of clause U, wherein the plurality of criteria includes length of G/C regions of the sequence of nucleotides, and the system further comprises: means for determining that a nucleotide included in the primer is a G or a C; means for determining that the nucleotide is included in a region of the primer that consists of one or more G's and one or more C's; means for determining a length of the region; and means for determining a score for a nucleotide based at least partly on the length of the region.

Clause Z. The system of clause U, wherein the plurality of criteria includes G/C content, and the system further comprises: determining a number nucleotides included in the primer that are G and C in relation to the total number of nucleotides included in the primer; and determining a score for the nucleotide based at least partly on the nucleotide being a G or a C and the number of nucleotides in the primer that are G or C in relation to the total number of nucleotides of the primer.

Clause AA. The system of clause U, wherein the plurality of criteria includes nucleotide differentiation, and the system further comprises: means for comparing a nucleotide of the primer with one or more additional nucleotides included in the primer; and means for determining a score for the nucleotide based at least partly on differences between the nucleotide and the one or more additional nucleotides.

Clause BB. The system of clause U, wherein the plurality of criteria includes primer similarity, and the system further comprises: means for comparing nucleotides of the primer with nucleotides of an additional primer; means for determining a number of nucleotides of the primer that are the same as the nucleotides of the additional primer and that are located in the same positions; and means for determining a score for the nucleotide based at least partly on the number of nucleotides of the primer that are the same as the nucleotides of the additional primer and that are located in the same positions.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for their particular cited teachings as well as for all that they disclose.

What is claimed is:

1. A method to improve the accuracy of random access of data stored in polynucleotide sequence data storage systems, the method comprising:
   (a) generating a group of primer sequences for use in generating polynucleotide sequences by:
   generating a plurality of primer nucleotide sequences;
   determining, for each of the plurality of primer nucleotide sequences, a respective score based at least partly on an estimated melting temperature and one or more additional criteria selected from the group comprising secondary structure formation, primer-dimer formation, length of A/T regions, length of G/C regions, G/C content, nucleotide differentiation, and primer similarity;
   combining the respective scores based on melting temperature and the one or more additional criteria into an aggregated score; and
   adding individual ones of the plurality of primer nucleotide sequences for which the aggregate score is less than a threshold score to the group of primer sequences;
   (b) generating a plurality of payload sequences that encode digital data;
   (c) determining for a one of the plurality of payload sequences from (b) and a primer target that is complementary to a one of the plurality of primer sequences from (a) that an amount of overlap between primer target and the one of the plurality of payload sequences is less than a threshold amount of overlap; and
   (d) generating a polynucleotide sequence that includes the primer target and the one of the plurality of payload sequences.

2. The method of claim 1, wherein determining the respective score at least partly on the one or more additional criteria includes:
   determining a respective score for individual nucleotides of an individual one of the plurality of primer nucleotide sequences; and
   combining the respective scores for the individual nucleotides to determine the respective score for the one or more additional criteria.

3. The method of claim 2, wherein the threshold score indicates a probability that an individual one of the plurality of primer nucleotide sequences affects the specificity of a polynucleotide sequence amplification operation.

4. The method of claim 1, wherein determining the respective score for each of the plurality of the primer nucleotide sequences based at least partly on the estimated melting temperature includes determining that the estimated melting temperature is included in a range of melting temperatures.

5. The method of claim 1, further comprising:
   determining for a one of the plurality of primer nucleotide sequences that the aggregate score is more than the threshold score;
   modifying at least one nucleotide of the one of the plurality of primer nucleotide sequences to produce a modified primer nucleotide sequence with an aggregate score that is less than the threshold score; and adding the modified primer nucleotide sequence to the group of primer sequences.

6. The method of claim 1, further comprising:
determining for a one of the plurality of payload sequences from (b) and a primer target that is complementary to a one of the plurality of primer sequences from (a) that an amount of overlap is more than the threshold amount of overlap; and
modifying one or more nucleotides of the primer target to reduce the amount of overlap.

7. A system to improve the accuracy of random access of data stored in polynucleotide sequence data storage systems, the system comprising:
a processing unit;
a memory in communication with the processing unit, the memory storing computer-readable instructions that when executed by the processing unit perform operations comprising:
(a) generating a group of primer sequences for use in generating polynucleotide sequences by:
generating a plurality of primer nucleotide sequences;
determining, for each of the plurality of primer nucleotide sequences, a respective score for each of a plurality of criteria related to a fitness of sequences of nucleotides to be used in polynucleotide sequence amplification and replication;
aggregating the respective scores for individual nucleotides of each respective one of the plurality of primer nucleotide sequences with respect to each of the plurality of criteria to produce scores for individual ones of the plurality of criteria and combining the scores for the individual ones of the plurality of criteria into an aggregated score; and
adding individual ones of the plurality of primer nucleotide sequences for which the aggregated score is less than a threshold score to the group of primer sequences;
(b) generating a plurality of payload sequences that encode digital data; and
(c) determining for a one of the plurality of payload sequences from (b) and a primer target that is complementary to a one of the plurality of primer nucleotide sequences from (a) that an amount of overlap between primer target and the one of the plurality of payload sequences is less than a threshold amount of overlap; and
(d) generating a polynucleotide sequence that includes the primer target and the one of the plurality of payload sequences.

8. The system of claim 7, wherein the plurality of criteria includes secondary structure formation; and the operations further comprise:
determining a score for a nucleotide of a one of the plurality of primer nucleotide sequences based at least partly on a probability of the nucleotide participating in the formation of a secondary structure.

9. The system of claim 7, wherein the plurality of criteria includes primer-dimer formation, and the operations further comprise:
determining a score for a nucleotide of a one of the plurality of primer nucleotide sequences based at least partly on a probability of the primer forming a dimer with another primer.

10. The system of claim 7, wherein the plurality of criteria includes length of A/T regions of the sequence of nucleotides, and the operations further comprise:
determining that a nucleotide included in a one of the plurality of primer nucleotide sequences is an A or a T;
determining that the nucleotide is included in a region of the one of the plurality of primer nucleotide sequences that consists of one or more A's and one or more T's;
determining a length of the region; and
determining a score for the nucleotide based at least partly on the length of the region.

11. The system of claim 7, wherein the plurality of criteria includes length of G/C regions of the sequence of nucleotides, and the operations further comprise:
determining that a nucleotide included in a one of the plurality of primer nucleotide sequences is a G or a C;
determining that the nucleotide is included in a region of a one of the plurality of primer nucleotide sequences that consists of one or more G's and one or more C's;
determining a length of the region; and
determining a score for the nucleotide based at least partly on the length of the region.

12. The system of claim 7, wherein the plurality of criteria includes G/C content, and the operations further comprise:
determining a number of nucleotides included in a one of the plurality of primer nucleotide sequences that are G and C in relation to a total number of nucleotides included in the one of the plurality of primer nucleotide sequences; and
determining a score for the nucleotide based at least partly on the nucleotide being a G or a C and the number of nucleotides included in the one of the plurality of primer nucleotide sequences that are G or C in relation to the total number of nucleotides of the one of the plurality of primer nucleotide sequences.

13. The system of claim 7, wherein the plurality of criteria includes nucleotide differentiation, and the operations further comprise:
comparing a nucleotide of a one of the plurality of primer nucleotide sequences with one or more additional nucleotides included in the one of the plurality of primer nucleotide sequences; and
determining a nucleotide differentiation score for the nucleotide based at least partly on differences between the nucleotide and the one or more additional nucleotides.

14. The system of claim 7, wherein the plurality of criteria includes primer similarity, and the operations further comprise:
comparing nucleotides of a one of the plurality of primer nucleotide sequences with nucleotides of an additional primer nucleotide sequence;
determining a number of nucleotides of the one of the plurality of primer nucleotide sequences that are the same as the nucleotides of the additional primer nucleotide sequence and that are located in the same positions; and
determining a score for the nucleotide based at least partly on the number of nucleotides of the one of the plurality of primer nucleotide sequences that are the same as the nucleotides of the additional primer nucleotide sequence and that are located in the same positions.

15. The system of claim 7, wherein generating the plurality of primer nucleotide sequences comprises generating primer nucleotide sequences with pseudo-random number algorithms.

16. A method to improve the accuracy of random access of data stored in polynucleotide sequence data storage systems, the method comprising:

(a) generating a group of primer sequences for use in generating polynucleotide sequences by:
  (i) determining one or more characteristics of a first primer sequence;
  (ii) determining a score for the first primer sequence based at least partly on the one or more characteristics in relation to one or more criteria, wherein the one or more criteria indicate a fitness of the first primer sequence to be utilized in polynucleotide sequence amplification and replication;
  (iii) determining that the score is less than a threshold score; and
  (iv) adding the first primer sequence to the group of primer sequences; and
  repeating steps (i) to (iv) to generate the group of primer sequences;
(b) generating a plurality of payload sequences that encode digital data;
(c) determining for a one of the plurality of payload sequences from (b) and a first primer target that is complementary to the first primer sequence from (a) that an amount of overlap between the first primer target and the one of the plurality of payload sequences is less than a threshold amount of overlap; and
(d) generating a polynucleotide sequence including the first primer target and the one of the plurality of payload sequences.

17. The method of claim 16, further comprising:
receiving, from a computing device, a request for digital data;
parsing a data structure to determine that the first primer sequence and a second primer sequence are associated with the digital data;
amplifying a polynucleotide included in a container of a polynucleotide storage system using a one or more enzymes, the first primer sequence, and the second primer sequence;
sequencing the polynucleotide to obtain a polynucleotide sequence;
decoding the polynucleotide sequence to identify a series of bits corresponding to the digital data; and
providing the series of bits to the computing device.

18. The method of claim 16, wherein the one or more characteristics includes melting temperature, wherein the one or more characteristics for the group of primer sequences is a first range of melting temperatures and the one or more characteristics for a second group of primer sequences is a second range of melting temperatures; and
further comprising:
storing polynucleotides generated with primer targets complementary to a primer included in the group of primer sequences in a first container; and
storing polynucleotides generated with primer targets complementary to a primer included in the second group of primer sequences in a second container.

19. The method of claim 16, wherein steps (i) to (iv) are repeated at least 100,000 times.

20. The method of claim 16, wherein the amount of overlap between the first primer target and the one of the plurality of payload sequences is determined by iteratively comparing regions of consecutive nucleotides of the one of the plurality of payload sequences with nucleotides of the first primer target.

* * * * *

SEQUENCE LISTING

```
<160> NUMBER OF SEQ ID NOS: 6

<210> SEQ ID NO 1
<211> LENGTH: 11
<212> TYPE: DNA
<213> ORGANISM: Artificial Sequence
<220> FEATURE:
<223> OTHER INFORMATION: A synthetic polynucleotide sequence

<400> SEQUENCE: 1
agcgttaagg g                                                          11

<210> SEQ ID NO 2
<211> LENGTH: 11
<212> TYPE: DNA
<213> ORGANISM: Artificial Sequence
<220> FEATURE:
<223> OTHER INFORMATION: A synthetic polynucleotide sequence

<400> SEQUENCE: 2
ctgctaggaa t                                                          11

<210> SEQ ID NO 3
<211> LENGTH: 11
<212> TYPE: DNA
<213> ORGANISM: Artificial Sequence
<220> FEATURE:
<223> OTHER INFORMATION: A synthetic polynucleotide sequence
```

-continued

```
<400> SEQUENCE: 3
ggagctccta c                                                              11

<210> SEQ ID NO 4
<211> LENGTH: 11
<212> TYPE: DNA
<213> ORGANISM: Artificial Sequence
<220> FEATURE:
<223> OTHER INFORMATION: A synthetic polynucleotide sequence

<400> SEQUENCE: 4
gctgatctga a                                                              11

<210> SEQ ID NO 5
<211> LENGTH: 11
<212> TYPE: DNA
<213> ORGANISM: Artificial Sequence
<220> FEATURE:
<223> OTHER INFORMATION: A synthetic polynucleotide sequence

<400> SEQUENCE: 5
agcttgcagg c                                                              11

<210> SEQ ID NO 6
<211> LENGTH: 11
<212> TYPE: DNA
<213> ORGANISM: Artificial Sequence
<220> FEATURE:
<223> OTHER INFORMATION: A synthetic polynucleotide sequence

<400> SEQUENCE: 6
ctggaactat g                                                              11
```